(12) United States Patent
Seare et al.

(10) Patent No.: US 7,222,079 B1
(45) Date of Patent: May 22, 2007

(54) METHOD AND SYSTEM FOR GENERATING STATISTICALLY-BASED MEDICAL PROVIDER UTILIZATION PROFILES

(75) Inventors: Jerry G. Seare, Sandy, UT (US); Patricia A. Smith-Wilson, Herriman, UT (US); Kurt Van Wagoner, Centerville, UT (US); Jean Andrea Mattey, Westlake, OH (US); Eileen K. Snyder, Sandy, UT (US); Candace C. Wahlstrom, Twin Falls, ID (US); Michelle Willis, Sandy, UT (US); Matthew R. Bentley, South Jordan, UT (US)

(73) Assignee: Ingenix, Inc., Eden Prairie, MN (US)

( * ) Notice: Subject to any disclaimer, the term of this patent is extended or adjusted under 35 U.S.C. 154(b) by 211 days.

(21) Appl. No.: 09/437,567

(22) Filed: Nov. 10, 1999

Related U.S. Application Data

(60) Continuation of application No. 08/539,413, filed on Oct. 5, 1995, now Pat. No. 6,223,164, which is a division of application No. 08/264,795, filed on Jun. 23, 1994, now Pat. No. 5,557,514.

(51) Int. Cl.
   *A61B 5/00* (2006.01)
   *G06F 19/00* (2006.01)
(52) U.S. Cl. ............................... 705/3; 705/2
(58) Field of Classification Search ................. 705/2–4
   See application file for complete search history.

(56) References Cited

U.S. PATENT DOCUMENTS

| | | |
|---|---|---|
| 3,566,365 A | 2/1971 | Rowson et al. |
| 3,697,957 A | 10/1972 | Barron |
| 3,716,840 A | 2/1973 | Maston |
| 4,286,330 A | 8/1981 | Isaacson |
| 4,290,114 A | 9/1981 | Sinay |
| 4,314,309 A | 2/1982 | Coli |
| 4,315,309 A * | 2/1982 | Coli ............................... 705/3 |
| 4,319,225 A | 3/1982 | Klose |
| 4,326,259 A | 4/1982 | Cooper et al. |
| 4,360,875 A | 11/1982 | Behnke |
| 4,368,059 A | 1/1983 | Doerges et al. |
| 4,435,769 A | 3/1984 | Nagano et al. |

(Continued)

OTHER PUBLICATIONS

"Creating a MEDPAR Analog to the RUG-III Classification System" Helath Care Financing Review/Winter 1994/vol. 16, No. 2, By Elizabeth Cornelius, B.S., Janet Feldman, and Korbin Liu, describes a Medicare payment system having data file and data codes for processing Medicare payment.*

(Continued)

*Primary Examiner*—Frantzy Poinvil
(74) *Attorney, Agent, or Firm*—Dorsey & Whitney, LLP

(57) ABSTRACT

A method and system for analyzing historical medical provider billings to statistically establish a normative utilization profile. Comparison of a medical provider's utilization profile with a normative profile is enabled. Based on historical treatment patterns and a fee schedule, an accurate model of the cost of a specific medical episode can be created. Various treatment patterns for a particular diagnosis can be compared by treatment cost and patient outcome to determine the most cost-effective treatment approach. It is also possible to identify those medical providers who provide treatment that does not fall within the statistically established treatment patterns or profiles.

1 Claim, 13 Drawing Sheets

U.S. PATENT DOCUMENTS

| | | | |
|---|---|---|---|
| 4,454,414 A | 6/1984 | Benton | |
| 4,479,176 A | 10/1984 | Grimshaw | |
| 4,491,725 A | 1/1985 | Pritchard | |
| 4,553,206 A | 11/1985 | Smutek et al. | |
| 4,632,428 A | 12/1986 | Brown | |
| 4,648,037 A | 3/1987 | Valentino | |
| 4,658,370 A | 4/1987 | Erman et al. | |
| 4,667,292 A | 5/1987 | Mohlenbrock et al. | |
| 4,700,297 A | 10/1987 | Hagel, Sr. et al. | |
| 4,731,725 A | 3/1988 | Suto et al. | |
| 4,733,354 A | 3/1988 | Potter et al. | |
| 4,803,641 A | 2/1989 | Hardy et al. | |
| 4,839,822 A | 6/1989 | Dormond et al. | |
| 4,858,121 A | 8/1989 | Barber et al. | |
| 4,866,634 A | 9/1989 | Reboh et al. | |
| 4,872,122 A | 10/1989 | Altschuler et al. | |
| 4,916,633 A | 4/1990 | Tychonievich et al. | |
| 4,945,476 A | 7/1990 | Bodick et al. | |
| 4,975,840 A | 12/1990 | DeTore et al. | |
| 4,987,538 A | 1/1991 | Johnson et al. | |
| 5,001,630 A | 3/1991 | Wiltfong | |
| 5,018,067 A | 5/1991 | Mohlenbrock et al. | |
| 5,065,315 A | 11/1991 | Garcia | |
| 5,070,452 A | 12/1991 | Doyle, Jr. et al. | |
| 5,225,976 A | 7/1993 | Tawil | |
| 5,235,702 A | 8/1993 | Miller | |
| 5,253,164 A | 10/1993 | Holloway et al. | |
| 5,255,187 A | 10/1993 | Sorensen | |
| 5,301,105 A | 4/1994 | Cummings, Jr. | |
| 5,307,262 A * | 4/1994 | Ertel | 705/2 |
| 5,324,077 A | 6/1994 | Kessler et al. | |
| 5,325,293 A | 6/1994 | Dorne | |
| 5,359,509 A | 10/1994 | Little | |
| 5,365,425 A | 11/1994 | Torma et al. | |
| 5,471,382 A | 11/1995 | Tallman et al. | |
| 5,486,999 A | 1/1996 | Mebane | |
| 5,508,912 A | 4/1996 | Schneiderman | |
| 5,517,405 A | 5/1996 | McAndrew et al. | |
| 5,519,607 A | 5/1996 | Tawil | |
| 5,521,814 A | 5/1996 | Teran et al. | |
| 5,544,044 A | 8/1996 | Leatherman | |
| 5,577,169 A | 11/1996 | Prezioso | |
| 5,583,758 A | 12/1996 | McIlroy et al. | |
| 5,594,637 A | 1/1997 | Eisenberg et al. | |
| 5,613,072 A | 3/1997 | Hammond et al. | |
| 5,644,778 A | 7/1997 | Burks et al. | |
| 5,652,842 A | 7/1997 | Siegrist, Jr. et al. | |
| 5,660,183 A | 8/1997 | Chiang et al. | |

OTHER PUBLICATIONS

"Chapter 12: Trends in Medicaid payments and users of covered services, 1975-91", Proquest, Health Care Financing Review, Washing: 1992.p. 235, 35 pages, describes a management information system and episode treatments.*

"Medicare home health: a description of total episodes of care", Proquest, Healthcare Financing, Washington: Summer 1993. vol. 14, Iss.4; p. 59, 16 pgs, describes an information management system on total episode cares.*

Leape, "Practice Guidelines and Standards: An Overview," *ORB* (Feb. 1990).

Jollis et al., "Discordance of Databases Designed for Claims Payment vs. Clinical Information Systems." *Annals of Internal Medicine* (Oct. 15, 1993).

Freed et al., "Tracking Quality Assurance Activity," *American College of Utilization Review Physicians* (Nov. 1988).

Roberts et al., "Quality and Cost Efficiency," *American College of Utilization Review Physicians* (Nov. 1988).

Rodriguez, "Literature Review," *Quality assurance and Utilization Review-Official Journal of the American College of Medical Quality* (Fall 1991).

Roos et al., "Using Administrative Data to Predict Important Health Outcomes," *Medical Care* (Mar. 1988).

Flagle et al., "AHCPR-NLM Joint Initiative for the Health Services Research Information, 1992 Update in OHSRI," *ORB* (Dec. 1992).

Elden, "The Direction of the Healthcare Marketplace." *Journal of the American College of Utilization review—official Journal of the American College of Medical Quality* (Fall 1991).

Burns et al., "The Use of Continuous quality Improvements in the Development and Dissemination of Medical Practice Guidelines," *QRB* (Dec. 1992).

Holzer, "The Advent of Clinical Standards for Professional Liability," *QRB* (Feb. 1990).

Horbas et al., "The Minnesota Clinical Comparison and Assessment Project," *QRB* (Feb. 1990).

Weiner et al., "Applying Insurance Claims Data to Assess Quality of Care: A Compilation of Potential Indicators," *QRB* (Dec. 1990).

Wakefield et al., "Overcoming the Barriers to Implementation of TQM/CQI in Hospitals: Myths and Realities," *QRB* (Mar. 1993).

Donabedian, "The Rule of Outcomes in Quality Assessment and Assurance," *QRB* (Nov. 1992).

Hadorn et al., "An Annotated Algorithm Approach to Clinical Guideline Development," *JAMA* (Jun. 24, 1992).

Falcone, et al., "the Critical Path Method in Stroke Rehabilitation: Lessons From an Experiment in Cost Containment and Outcome Improvement," *QRB* (Jan. 1993).

Reinertsen, "Outcomes Management and Continuous Quality Improvement: the Compass and the Rudder," *QRB* (Jan. 1993).

Mennemeyor, "Downstream Outcomes: Using Insurance Claims Data to Screen for Errors in Clinical Laboratory Testing," *QRB* (Jun. 1991).

Fezzoni., "Using Severity Information for Quality Assessment: A Review of Three Cases by Five Severity Measures," *QRB* (Dec. 1989).

Kahn, "Measuring the Clinical Appropriateness of the Use of a Procedure: Promise or Panacea?," *The Journal of Family Practice* (1993).

Lawless, "A Managed Care Approach to Outpatient Review," *Quality Assurance and Utilization Review-Official Journal of the American College of Utilization Review Physicians* (May 1990).

Dragalin et al., "Institutes for Quality: Prudential's Approach to Outcomes Management for Specialty Procedures," *QRB* (Mar. 1990).

Chinsky., Patterns of Treatment Ambulatory Health Care Management, Physician Profiling—The Impact of Physician, Patient, and Market Characteristics on Appropriateness of Physician Practice in the Ambulatory Setting (Doctoral Dissertation, the University of Michigan, 1991).

Report on Medical Guidelines Outcome Research, 4(Feb. 11, 1993).

Homer et al., Accuracy of patient encounter and patient billing information in ambulatory care, Journal of Family Practice, vol. v33, Issue: n6 p. 593(6), Dec. 1991.

"Practice Guidelines—the Experience of Medical Specialty Societies.l" *U.S. Govt Q Report to Congressional Requestors (QAO/PCDM-91-11 Practice Guideline)* (Feb. 21, 1991).

"Medicare intermediary Manual Part 3—Claims Process," Department of H&H's. Health Care Financing Administration, Transmittal No. 1595 (Apr. 1993).

CCH Pulse The Health Care Reform Newsletter (Apr. 1993).

"Implementation Guide" *Patterns of Treatment Ambulatory Health Care Management,* Pub. by Concurrent Review Technology Inc.

"Physician Profiling," *Patterns of Treatment Ambulatory Healthcare Management,* Pub. by Concurrent Review Technology Inc.

"Pattern Processing Model." *Patterns of Treatment Ambulatory Healthcare Management.* Pub. by Concurrent Review Technology Inc.

Winslow, "Report Card on Quality and Efficiency of HMO May Provide a Model for Others," *The Wall Street Journal*.

Jenks., "Strategies for Reforming Medicare's Physician Payments, Physician Diagnosis—Related Groups and Other Approaches." *The New England Journal of Medicine* (Jun. 6, 1985).

Solon et al., "Delineating Episodes of Medical Care" *AJPH* (Mar. 1967).

*Medical Care*, Sep. 1986 vol. 24 #9, Supplement.

Miller et al., "Physician Charges in the Hospital," *Medical Care* Jul. 1992, vol. 30, #7.

Garnick et al., "Services and Charges by PPO Physicians for PPO and Indemnity Patients," *Medical Care* Oct. 1990, vol. 28 (10).

Hurwiez et al., "Care Seeking for Musculo-Skeletal and Respiratory Episodes in a Medicare Population," *Medical Care*, Nov. 1991, vol. 29 (11).

Gold et al., "The Content of Adult Primary Care Episodes," *Public Health Reports*. Jan.-Feb. 1982.

Welch et al., "Geographic Variation in expenditures for Physician's Services in the U.S.," *New England Journal of Medicine* Mar. 4, 1993 vol. 328 (9).

Schneeweiss, "Diagnosis Clusters: A New Tool for Analyzing the Content of Ambulatory Medical Care." *Medical Care* Jan. 1983.

Schowstack et al., "Episode of Care Physician Payment: A Study of Coronary Bypass Care Graft Surgery," *Inquiry*, vol. 24, 1987.

Schoffert, "National Ambulatory Medical Care Survey: 1989 Summary," *Vital and Health Statistics*. Apr. 1992, Series 13. #110.

Graves, "Detailed Diagnosis and Procedures, National Hospital Discharge Survey, 1990," *Vital and Health Statistics*. Jun. 1992, Series 13. #113.

"National Hospital Discharge Survey: Annual Summary 1990," *Vital and Health Statistics,* Jun. 1992, Series 13, #112.

"Prevalence of Selected Chronic Conditions: United States 1986-88," *Vital and Health Statistics*. Feb. 1993, Series 10, #182.

"Current Estimates From the National Health Interview Survey, 1991," *Vital and Health Statistics*. Dec. 1992, Series 10, #184.

Lezzon et al., "A Description and Clinical Assessment of the Computerized Severity Index," *QRB* Feb. 1992.

*Healthcare Financing Review*, Winter, 1991, vol. 13, #2, p. 30.

*Statistical Abstracts of the United States*, 1992.

*Health and Prevention Profile United States*, 1991.

"Press Release," *Health Outcomes Institute* Feb. 8, 1993.

MDR Outlook, vol. 4 (3).

Weingarten et al., "The Case for Intensive Dissemination: Adoption of Practice Guidelines in the Coronary Care Unit," *QRB*. Dec. 1992.

Dolan et al., "Using the Analytic Hierarchy Practice (AHP) to Develope and Disseminate Guideline," *QRB* Dec. 1992.

Margolis et al., "Profiling Practice Patterns for Clinical Benchmarking," *GHAA Institute* Jun. 14, 1993.

Froed et al., "Tracking Quality Assurance Activity," *American College of Utilization Review Physicians*. Nov. 1988.

Roberts et al., "Quality and cost Efficiency The Evidence for Channeling," *American College of Utilization Review Physicians*. Nov. 1988.

"IHQ Quality First Health Care Practice Guidelines by Specialty," *Institute for Healthcare Quality*, 1993.

Intel: Med Advertisement.

*Report on Medical Guidelines and Outcome Research*, Feb. 11, 1993.

Wall., "Practice Guidelines: Promise or Panacea," *The Journal of Family Practice*, vol. 37 (1), 1993.

HBO Patient Care Software Article.

*Federal Register*, vol. 57 (170) Sep. 1, 1992, pp. 39879-39893.

*Federal Register*, vol. 57 (167) Aug. 27, 1992, pp. 38845-38847.

Gottlieb et al., "Clinical Practice Guidelines at an HMO: Development and Implementation in a Quality Improvement Model," *QRB* (Feb. 1990).

Dialog File 73, Acc. No. 611097, Div. Raid. Res. Inst. Brain Blood Vessels, Akita, "A Computer Processing System for Patient Records of Cerebro Vascular Disease, Emphasizing the Retrieval of Radiological Examinations," 1975 pgs (563-571).

Dialog File 149, Acc. No. 13228972, Addtion Letter: V8, Issue No. 11, "The Baltimore County of Substance Abuse Uses a Customized Model for Data Collection and Billing System," Nov. 1992 pg (3).

Dialog File 149, Acc. No. 10475237, Hughes et al., Health Care Financing Review, "Procedure Codes: Potential Modifiers of Diagnosis Related Groups," V12, Issue No. 1, Fall 1990.

Dialog File 149, Acc No. 1198663, Journal of Family Practice, "Accuracy of Patient Encounter and Billing Information in Ambulatory Care," V33 Issue No. 6, Dec. 1991.

Dialog File 15, Acc. No. 00723419, Chithelen, "A Health Opportunity," Forbes, V14 Issue No. 3, Feb. 3, 1992, pp. 46-47.

Dialog File 751, Acc. No. 00253707, "Medical Records Management System (MRMS)," Information of Florida. Jan. 1992.

Dialog File 275, Acc. No. 01237169, Steingerg, D., "Whiplash Again? Dr. Database Will Be With You in Just a Moment. (The National Health Care Anti-Fraud Association)," PC Week, V5, Issue No. 2, Jan. 12, 1988, p. 5(1).

Dialog File 149, Acc. No. 08726638, Bailey, N.C., "how to Control Overcharging By Physicians: Unnecessary Payments to MD's that Were Caused by Inaccurate Coding on Claims That Cost Payers Billions Last Year. Here's a Way to Combat This," Business and Health, V* Issue No. 8, Aug. 1990, p. 13(5).

Dialog File 149, Acc. No. 15781211, Borzo G., "SmartBombing Fraud: Insurers Turn to Powerful New Computers to Spot Aberrant Claims," American Medical News, V37, No. 38, Oct. 10, 1994, p. 3(4).

Dialog File 149, Acc. No. 09374757, Mellrath, S., "Medicare to Begin Evaluation of Physician Practice Patterns," American Medical News, V33. No. 32, Aug. 24, 1990.

Rosko., "DRG's and Severity of Illness Measures: An Analysis of Patient Classification System." *Journal of Medical Systems*, Nov. 1988, vol. 12.

McMahon et al., "Measurement of Severity of Illness and the Medicare Prospective Payment System," *Journal of General Internal Medicine*. Sep./Oct. 1988, vol. 3.

Couch et al., "Severity of Illness Measures: Opportunities of Clinicians." *Annals of Internal Medicine*, (Nov. 1988).

"Clinical Classification for Health Policy Research: Discharge Statistics by Principle Diagnosis and Procedure," U.S. Department of Health and Human Services, Provider Studies Research Note No. 17 (Aug. 1993).

* cited by examiner

METHOD AND SYSTEM FOR GENERATING STATISTICALLY-BASED MEDICAL PROVIDER UTILIZATION PROFILES

This application is a Continuation of application Ser. No. 08/539,413, filed Oct. 5, 1995, now U.S. Pat. No. 6,223,164 which is a Divisional of application Ser. No. 08/264,795, filed Jun. 23, 1994, which issued as U.S. Pat. No. 5,557,514 on Sep. 17, 1996 application(s) are incorporated herein by reference.

MICROFICHE APPENDIX

This specification includes a Microfiche Appendix which includes I page of microfiche with a total of 37 frames. The microfiche appendix includes computer source code of one preferred embodiment of the invention. In other embodiments of the invention, the inventive concept may be implemented in other computer code, in computer hardware, in other circuitry, in a combination of these, or otherwise. The Microfiche Appendix is hereby incorporated by reference in its entirety and is considered to be a part of the disclosure of this specification.

I. BACKGROUND OF THE INVENTION

A. Field of the Invention

The invention relates to methods and systems for analyzing medical claims histories and billing patterns to statistically establish treatment utilization patterns for various medical services. Data is validated using statistical and clinically derived methods. Based on historical treatment patterns and a fee schedule, an accurate model of the cost of a specific medical episode can be created. Various treatment patterns for a particular diagnosis can be compared by treatment cost and patient outcome to determine the most effective treatment approach. It is also possible to identify those medical providers who provide treatment that does not fall within the statistically established treatment patterns or profiles.

B. The Background Art

It is desirable to compare claims for reimbursement for medical services against a treatment pattern developed from a large body of accurate medical provider billing history information. Although in the prior art some attempt was made to compare claims for reimbursement for medical services to a normative index, the prior art did not construct the normative index based on actual clinical data. Rather, the prior art based the normative index on a subjective conception (such as the medical consensus of a specialty group) of what the proper or typical course of treatment should be for a given diagnosis. Such prior art normative indices tended to vary from the reality of medical practice. In the prior art, automated medical claims processing systems, systems for detecting submission of a fraudulent medical claims, and systems for providing a medical baseline for the evaluation of ambulatory medical services were known. Documents which may be relevant to the background of the invention, including documents pertaining to medical reimbursement systems, mechanisms for detecting fraudulent medical claims, and related analytical and processing methods, were known. Examples include: U.S. Pat. No. 4,858,121, entitled "Medical Payment System" and issued in the name Barber et al. on Aug. 15, 1989; U.S. Pat. No. 5,253,164, entitled "System and Method for Detecting Fraudulent Medical Claims Via Examination of Service Codes" and issued in the name of Holloway et al. on Oct. 12, 1993; U.S. Pat. No. 4,803,641, entitled "Basic Expert System Tool" and issued in the name of Hardy et al. on Feb. 7, 1989; U.S. Pat. No. 5,658,370, entitled "Knowledge Engineering Tool" and issued in the name of Erman et al. on Apr. 14, 1987; U.S. Pat. No. 4,667,292, entitled "Medical Reimbursement Computer System" and issued in the name of Mohlenbrock et al. on May 19, 1987; U.S. Pat. No. 4,858,121, entitled "Medical Payment System" and issued in the name of Barber et al. on Aug. 15, 1989; and U.S. Pat. No. 4,987,538, entitled "Automated Processing of Provider Billings" and issued in the name of Johnson et al. on Jan. 22, 1991, each of which is hereby incorporated by reference in its entirety for the material disclosed therein.

Additional examples of documents that may be relevant to the background of the invention are: Leape, "Practice Guidelines and Standards: An Overview," *QRB* (February 1990); Jollis et al., "Discordance of Databases Designed for Claims Payment versus Clinical Information Systems," *Annals of Internal Medicine* (Oct. 15, 1993); Freed et al., "Tracking Quality Assurance Activity," *American College of Utilization Review Physicians* (November, 1988); Roberts et al., "Quality and Cost-Efficiency," *American College of Utilization Review Physicians* (November, 1988), Rodriguez, "Literature Review," *Quality Assurance and Utilization Review—Official Journal of the American College of Medical Quality* (Fall 1991); Elden, "The Direction of the Healthcare Marketplace," *Journal of the American College of Utilization Review Physicians* (August 1989); Rodriguez, "Literature Review," *Quality Assurance and Utilization Review—Official Journal of the American College of Medical Quality* (Fall 1991); Roos et al., "Using Administrative Data to Predict Important Health Outcomes," *Medical Care* (March 1988); Burns et al., "The Use of Continuous Quality Improvement Methods in the Development and Dissemination of Medical Practice Guidelines, *QRB* (December, 1992); Weingarten, "The Case for Intensive Dissemination: Adoption of Practice Guidelines in the Coronary Care Unit," *QRB* (December, 1992); Flagle et al., "AHCPR-NLM Joint Initiative for Health Services Research Information: 1992 Update on OHSRI," *QRB* (December, 1992); Holzer, "The Advent of Clinical Standards for Professional Liability," *QRB* (February, 1990); Gottleib et al., "Clinical Practice Guidelines at an HMO: Development and Implementation in a Quality Improvement Model," *QRB* (February, 1990); Borbas et al., "The Minnesota Clinical Comparison and Assessment Project," *QRB* (February, 1990); Weiner et al., "Applying Insurance Claims Data to Assess Quality of Care: A Compilation of Potential Indicators," *QRB* (December, 1990); Wakefield et al., "Overcoming the Barriers to Implementation of TQM/CQI in Hospitals: Myths and Realities," *QRB* (March, 1993); Donabedian, "The Role of Outcomes in Quality Assessment and Assurance," *QRB* (November, 1992); Dolan et al., "Using the Analytic Hierarchy Process (AHP) to Develop and Disseminate Guidelines," *QRB* (December, 1992); Hadorn et al., "An Annotated Algorithm Approach to Clinical Guideline Development," *JAMA* (Jun. 24, 1992); Falconer et al., "The Critical Path Method in Stroke Rehabilitation: Lessons from an Experiment in Cost Containment and Outcome Improvement," *QRB* (January, 1993); Reinertsen, "Outcomes Management and Continuous Quality Improvement: The Compass and the Rudder," *QRB* (January, 1993); Mennemeyer, "Downstream Outcomes: Using Insurance Claims Data to Screen for Errors in Clinical Laboratory Testing," *QRB* (June, 1991); Iezzoni, "Using Severity Information for Quality Assessment: A Review of Three Cases by Five Severity Measures," *QRB* (December 1989); Kahn, "Measuring the Clinical Appropriateness of the Use of a Procedure," *Medical Care* (April, 1988); Wall, "Practice Guidelines: Promise or Panacea?," *The Journal of Family Practice* (1993); Lawless, "A Managed Care Approach to Outpatient Review," *Quality Assurance and Utilization Review—Official Journal of the American College of Utilization Review Physicians* (May, 1990); Dragalin et al., "Institutes for Quality: Prudential's Approach to Outcomes Management for Specialty Procedures," *QRB* (March, 1990); Chinsky, "Patterns of Treatment Ambulatory Health Care Management, Physician Profiling—The Impact of Physician, Patient, and Market Characteristics On Appropriateness of Physician Practice in the Ambulatory Setting," (Doctoral Dissertation, The University of Michigan, 1991), published by Concurrent Review Concurrent Review Technology, Inc., Shingle Springs, California; "Patterns of Treatment Ambulatory Health Care Management, Implementation Guide," published by Concurrent Review Concurrent Review Technology, Inc., Shingle Springs, California; "Patterns of Treatment Ambulatory Health Care Management, Patterns Processing Model," published by Concurrent Review Concurrent Review Technology, Inc., Shingle Springs, California; *Report on Medical Guidelines & Outcome Research*, 4 (Feb. 11, 1993); "Practice Guidelines—The Experience of Medical Specialty Societies," *United States General Accounting Office Report to Congressional Requestors* (*GAO/PEMD*-91-11 *Practice Guideline*) (Feb. 21, 1991); "Medicare Intermediary Manual Part 3—Claims Process," *Department of Health and Human Services, Health Care Financing Administration, Transmittal No.* 1595 (April 1993); *CCH Pulse The Health Care Reform Newsletter* (Apr. 19, 1993); Winslow, "Report Card on Quality and Efficiency of HMOs May Provide a Model for Others," *The Wall Street Journal*; Jencks et al., "Strategies for Reforming Medicare's Physician Payments," *The New England Journal of Medicine* (Jun. 6, 1985); Solon et al., "Delineating Episodes-of Medical Care," *A.J.P.H.* (March, 1967); *Health Care* (September, 1986) (the entire issue of Volume 24, Number 9, Supplement); Miller et al., "Physician Charges in the Hospital," *Medical Care* (July, 1992); Garnick, "Services and Charges by PPO Physicians for PPO and Indemnity Patients," *Medical Care* (October, 1990); Hurwicz et al., "Care Seeking for Musculoskeletal and Respiratory Episodes in a Medicare Population," *Medical Care* (November, 1991), Gold, "The Content of Adult Primary Care Episodes," *Public Health Reports* (January–February, 1982); Welch et al., "Geographic Variations in Expenditures for Physicians' Services in the United States," *The New England Journal of Medicine* (Mar. 4, 1993); Schneeweiss et al., "Diagnosis Clusters: A New Tool for Analyzing the Content of Ambulatory Medical Care," *Medical Care* (January, 1983); Showstack, "Episode-of-Care Physician Payment: A Study of Coronary Arter Bypass Graft Surgery," *Inquiry* (Winter, 1987); Schappert, "National Ambulatory Medical Survey: 1989 Summary," *Vital and Health Statistics, U.S. Department of Health and Human Services, Public Health Service, Centers for Disease Control, National Center for Health Statistics* (April, 1992) (DHHS Publication No. [PHS] 92-1771); Graves, "Detailed Diagnoses and Procedures, National Hospital Discharge Survey, 1990," *Vital and Health Statistics, U.S. Department of Health and Human Services, Public Health Service, Centers for Disease Control, National Center for Health Statistics* (June, 1992) (DHHS Publication No. [PHS] 92-1774); "National Hospital Discharge Survey: Annual Summary, 1990," *Vital and Health Statistics, U.S. Department of Health and Human Services, Public Health Service, Centers for Disease Control, National Center for Health Statistics* (June, 1992) (DHHS Publication No. [PHS] 92-1773); "Prevalence of Selected Chronic Conditions: United States, 1986–88," *Vital and Health Statistics, U.S. Department of Health and Human Services, Public Health Service, Centers for Disease Control, National Center for Health Statistics* (February, 1993) (Series 10, No. 182); "Current Estimates From the National Health Interview Survey, 1991," *Vital and Health Statistics, U.S. Department of Health and Human Services, Public Health Service, Centers for Disease Control, National Center for Health Statistics* (February, 1993) (DHHS Publication No. [PHS] 93-1512); Iezzoni et al., "A Description and Clinical Assessment of the Computerized Severity Index," *QRB* (February, 1992); *Health Care Financing Review*, p. 30 (Winter, 1991); *Statistical Abstract of the United States* (1992); and *Health and Prevention Profile—United States* (1991) (published by U.S. Department of Health and Human Services, Public Health Service, Centers for Disease Control, National Center for Health Studies), each of which is hereby incorporated by reference in its entirety for the material disclosed therein.

Additional background materials to which the reader is directed for both background and to refer to while studying this specification include: *Physicians'Current Procedural Terminology CPT '94*, published by American Medical Association, *Code it Right Techniques for Accurate Medical Coding*, published by Medicode Inc., *HCPCS 1994 Medicare's National Level II Codes*, published by Medicode Inc., *Med-Index ICD 9 CM Fourth Edition* 1993, published by Med-Index, each of which is hereby incorporated by reference in its entirety for the material disclosed therein.

II. Summary of the Invention

It is an object to provide a mechanism for assessing medical services utilization patterns. The invention achieves this object by allowing comparison processing to compare an individual treatment or a treatment group against a statistical norm or against a trend.

It is an object of the invention to provide a mechanism for converting raw medical providers' billing data into a database. The invention achieves this object by read, analyze and merge ("RAM") processing coupled with claims edit processing to achieve a reliable, relevant data set.

It is an object of the invention to provide a mechanism for accurately determining an episode of care. The invention achieves this object by providing a sequence of steps which, when performed, yield an episode of care while filtering out irrelevant and inapplicable data.

It is an object of the invention to provide a method for performing a look-up of information, that is, providing a mechanism for gaining access to different parts of the informational tables maintained in the database. This object is achieved by reviewing the referenced tables for specific codes representing specific diagnoses. The codes are verified for accuracy. Then tables are accessed to display selected profiles. Users are then given the opportunity to select profiles for comparison.

It is an object of the invention to provide a method for comparing profiles. This object is achieved by comparing index codes against historical reference information. Discovered information is checked against defined statistical criteria. The process is repeated for each index code and its profiles developed in the history process as many times as necessary to complete the information gathering.

It is an object of the invention to create, maintain and present to the user a variety of report products. These reports are provided either on-line or in a hard copy format. The process of creating, maintaining and presenting these reports is designed to present relevant information in a complete and useful manner.

It is an object of the invention to provide a mechanism for creating a practice parameter database. This object is achieved in the invention by repetitive episode of care processing and entry of processed episode of care data into a data table until the populated data table becomes the practice parameter database.

III. BRIEF DESCRIPTION OF THE DRAWINGS

IV. DETAILED DESCRIPTION OF THE PREFERRED EMBODIMENT

Figure 1:
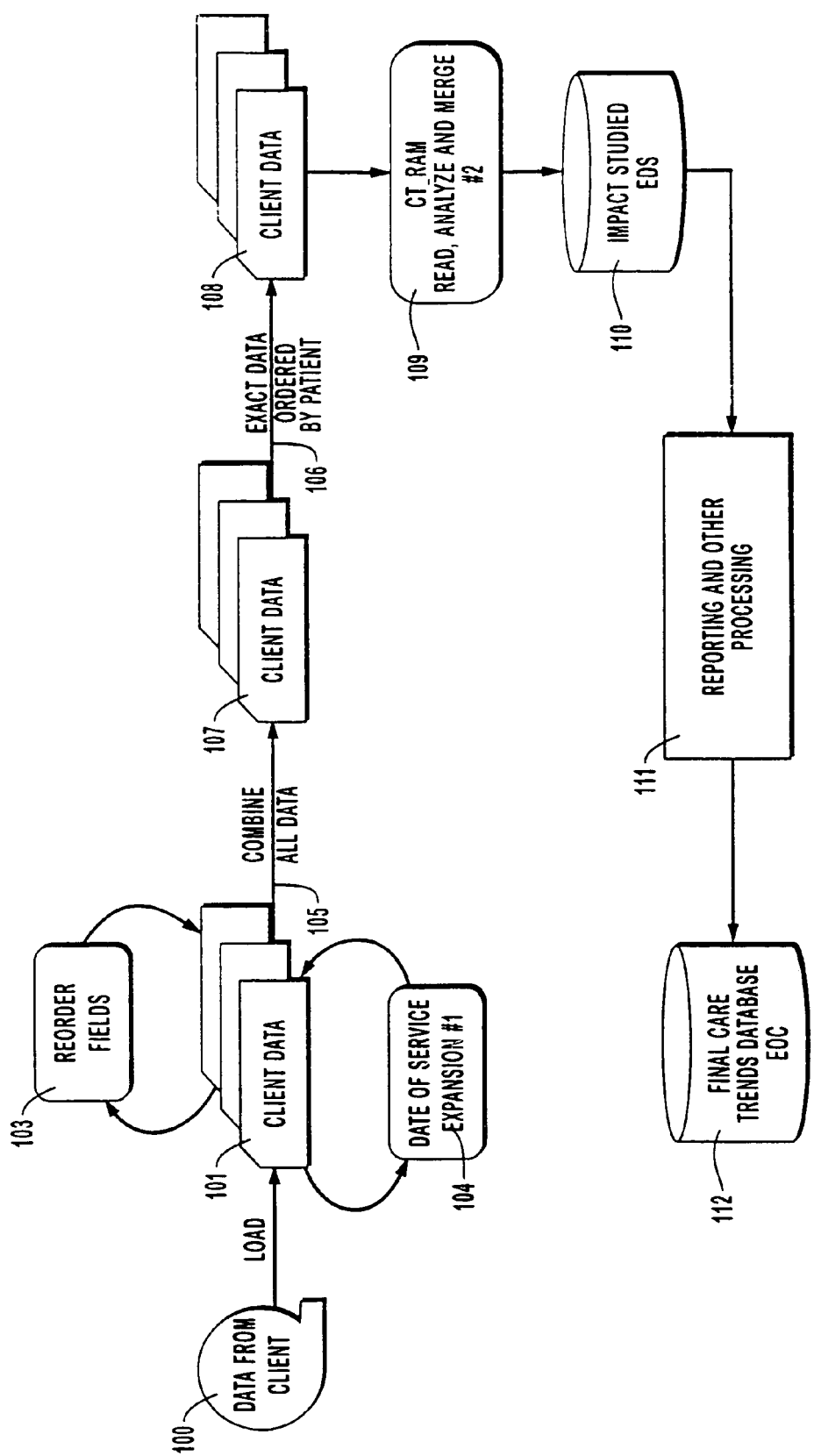
FIG. 1 depicts steps performed in the method of the invention to establish a practice parameter or utilization profile for a particular diagnosis.

The invention includes both a system and a method for analyzing healthcare providers' billing patterns, enabling an assessment of medical services utilization patterns. When the invention is employed, it can readily be seen whether a provider or multiple providers are overutilizing or underutilizing services when compared to a particular historical statistical profile. The statistical profiles of the invention are a statically-derived norms based on clinically-validated data which has been edited to eliminate erroneous or misleading information. The profiles may be derived from geographic provider billing data, national provider billing data, the provider billing data of a particular payor entity (such as an insurance company) or various other real data groupings or sets. Multiple informational tables are used in the database of the preferred embodiment of the invention. These include a Procedure Description Table, ICD-9 Description Table, Index Table, Index Global Table, Index Detail Table, Window Table, Procedure Parameter Table, Category Table, Qualifying Master Table, Specialty Table, Zip/Region Table, Specialty Statistic Table, Age/Gender Statistic Table, Region Statistic Table, Qualifying Index Table, Qualifying Group Table, Category Parameter Table, and Duration Parameter Table. ICD 9 codes or ICD (International Classification of Diseases, generically referred to as a disease classification) codes as they are generally referred to herein are used in the preferred embodiment. In other embodiments of the invention other codes could be used, such as: predecessors or successors to ICD codes or substitutes therefor, such as DSM 3 codes, SNOWMED codes, or any other diagnostic coding schemes. These tables are described in detail as follows. It should be noted, however, that these tables described are used by the inventors in one implementation of the invention, and that the inventive concept described herein may be implemented in a variety of ways.

Procedure Description Table

This table identifies and validates five years of both CPT (Current Procedural Terminology, generically referred to as an identifying code for reporting a medical service) and HCPCS level II procedure codes. The lifetime occurrence maximum and follow-up days associated with a procedure code are also located in this table.

| Code (Key) | Alpha/Numeric | 5 | Standard CPT or HCPCS (5 Years including Modifiers) |
|---|---|---|---|
| Sub-Code | Character | 2 | * = Starred Procedures<br>N = New Codes Current Year<br>D1 = Deleted Code Current Year<br>D2 = Deleted Code Previous Year<br>D3 = Deleted Code Third Year<br>D4 = Deleted Code Fourth Year<br>C = Changed Description |
| Life Time Occurence | Numeric | 2 | Number = Count of occurrence in a lifetime<br>Blank = Not applicable |
| Follow Up Days | Numeric | 3 | Number of Follow up Days to procedure. |
| Description | Character | 48 | Standard abbreviated description |
| Total | | 60 | |

USE:
 This table can validate CPT and HCPCS codes.
 Five years of codes will be kept.
 Give a brief description of the code.
 Gives the maximum number of occurrences that this code can be done in a lifetime, if applicable. (Programming not addressed, to date)
 Give the number of follow up days to a procedure. (Programming not addressed, to date)
 Modifiers are stored in this table with a "099" prefix (i.e., the 80 modifier is "09980") with a description of the modifier.
 This table interrelates with:
  Parameter Tables
  Category Table
  Qualifying Tables
  Specialty Table
  CPT Statistic Table

ICD-9 Description Table

This table identifies and validates five years of diagnosis codes. It also contains a risk adjustment factor for each diagnosis.

| ICD-9 Code (Key) | Alpha/Numeric | 5 | Left justified, assumed decimal after 3rd position |
|---|---|---|---|
| Sub-Code | Character | 2 | N = New Code<br>D = Deleted Code<br>C = Changed Code |

-continued

| | | | |
|---|---|---|---|
| Indicator | Character | 1 | * or blank<br>* = code requires 4th and/or 5th digits to be specific |
| Risk | Alpha/Numeric | 2 | Overall Classification of Disease |
| Description | Character | 48 | Standard abbreviated description |
| Total | | 58 | |

USE:
    This table can validate ICD codes.
    Five years of codes will be kept.
    Give a brief description of the code.
    Show if the code is incomplete and in need of a fourth or fifth digit. An ICD code which should have a 4th and/or 5th digit is listed with an "*".
    This file interrelates with:
      Index Table
      Index Detail Table
      Index Global Table
      Qualifying Master Table
      Family Table
      All Parameter Tables

Index Detail Table

This table identifies ICD-9 codes relevant to each specific index code and is used to drive the search for each episode of care. ICD-9 codes have been given an indicator which determines whether or not the associated CPT code should be included in the episode of care. Also, an indicator may cause exclusion of any specific patient record from an episode of care analysis.

| | | | |
|---|---|---|---|
| Index Code | Alpha/Numeric or character | 5 | Left justified assumed decimal after 3rd position. |
| Indicator | Character | 2 | I = Index code<br>R = Related<br>S = signs/symptoms<br>RO = Rule out<br>C = complications (exclude)<br>M = miscoded<br>V = Vcodes<br>MI = Miscoded Index |
| Beg-ICD | Alpha/Numeric | 5 | ICD-9 Beginning Range Code |
| End-ICD | Alpha/Numeric | 5 | ICD-9 Ending Range Code |
| Update | Character | 1 | A, C, or Blank |
| Total | | 17 | |

USE:
    This table drives the search for the Episode of Care (EOC) and is keyed off the Index Code field.
    Other codes to be included in the parameter search are specified in the indicator field.
    ICD codes with an indicator of "C" when found in a patient history will disqualify the entire patient from the EOC process.
    "Some Index Codes are listed in part with "?" and "??" to exhibit that it does not matter what the trailing 4th and/or 5th digit is, the record is to be accessed for the parameter. For example, the Index code may be 701??, meaning that if the first three digits of the ICD code start with 701 then use the code regardless of what the 4th and/or 5th digit may be."

ICD codes maintained in this table are listed as complete as verified by the ICD description table, with the exception of ICD codes beginning with an indicator of "M". Programming logic should consider this when using "M" codes in the search process.

This table is used for drafting and populating a temporary file built from this table and the Index Global Table based on indicators and keys extrapolated from the Index table.

Program Logic to Assign Episode of Care

Any patient history with an ICD from the temp file for the chosen Index code is tagged for possible assignment of Episode of Care.

Perform a search on patient history for any ICD code from temp file with an indicator of "C". If found, exclude entire patient history from EOC search.

The qualifying tables are accessed to verify if specific qualifying factors apply to determine if patient history meets criteria for determination of valid episode of care. (See Qualifying Tables for further explanation)

The qualifying table is then accessed for further delineation of qualifying circumstances by EOC.

A timeline is tracked, by patient, for all potential Episodes of care that may occur for a given patient history.

The data is arrayed based on profile classes which are eight subsets of Procedure categories. An aggregate of all procedures can also be reported. (See Category Table for further explanation)

This table interrelates with:
    ICD Description Table
    Index Table
    Index Global Table
    Parameter Table
    CPT Statistic Table
    Age/Sex Table

Index Table

This table provides a preliminary step for assigning and accessing different tables during the Episode of Care process. This table houses the assignment of staging and whether or not the Index Global table should be accessed.

| | | | |
|---|---|---|---|
| Index Code | Alpha/Numeric | 5 | Left justified assumed decimal after 3rd position. |
| Staging | Character | 2 | P = preventive<br>A = acute<br>C = chronic<br>L = life threatening<br>M = manifestations |
| Global Key | Alpha | 2 | C = complications<br>M1 = miscoded medical vcodes<br>M2 = miscoded surgical vcodes<br>1 = medical vcodes<br>2 = surgical vcodes |
| Indicator | Character | 2 | C = complications<br>V = vcodes |
| Update | Character | 1 | A, C, or Blank |
| Total | | 12 | |

USE:
  Once an Index code has been selected, this table is searched for whether or not the global index table needs to be accessed.
  This table assigns the staging for the index code which points to the window table.
  This table interrelates with:
    ICD Description Table
    Index Detail Table
    Index Global Table
    Window Table Index Global Table This table gives a listing of ICD-9 codes common to most Index codes for either inclusion in an EOC such as preventive or aftercare, or exclusion of a patient history such as medical complications.

| | | | |
|---|---|---|---|
| GLOBAL KEY | Alpha/Numeric | 2 | C = complications |
| | | | M1 = miscoded medical vcodes |
| | | | M2 = miscoded surgical vcodes |
| | | | 1 = medical vcodes |
| | | | 2 = surgical vcodes |
| ICD Beginning | Alpha/Numeric | 5 | ICD-9 Beginning range code |
| ICD Ending | Alpha/Numeric | 5 | ICD-9 Ending range code |
| Update | Character | 1 | A, C, or Blank |
| Total | | 13 | |

USE:
  This table is used to identify a generic V Code or complication ICD code to be used in an EOC search for any Index code.
  It is triggered by the Index table.
  The surgical Vcodes include all M1, M2, 1 and 2's.
  Medical Vcodes include M1 and 1.
  A complication ICD code will negate the use of a patient history from the EOC search.
  A temporary file for the index code is created based on ICDs extrapolated from this table as well as the Index detail table
  This table interrelates with:
    ICD Description Table
    Index Table
    Index Detail Table Window Table This table contains the time period preceding and following an episode of care that must be present without any services provided to the patient relating to the index code or associated codes. These windows are used to define the beginning and end points of an episode of care. This table is driven from the staging field in the index table.

| | | | |
|---|---|---|---|
| Index Code | Alpha/Numeric | 5 | Left justified assumed decimal after 3rd position |
| Staging Indicator | Character | 2 | P = Preventive |
| | | | C = Chronic, A = Acute |
| | | | L = Life threatening, |
| | | | M = Manifestation |
| Beginning Window | Numeric | 3 | Time Period for no occurrence of ICD for Index Code |
| Ending Window | Numeric | 3 | Time Period for no occurrence of ICD for Index Code |
| Update | Character | 1 | A, C, or Blank |
| Total | | 9 | |

USE:
  This table is keyed off of the staging indicator and it tells the program how long of a "Clear Window" is needed on both ends of this EOC for it to be valid.

Procedure Parameter Table

This table contains the specific CPT codes identified for each index code listed chronologically with associated percentiles, mode, and average.

| | | | |
|---|---|---|---|
| Index Code | Alpha/Numeric | 5 | Left justified assumed decimal after 3rd position |
| Profile | Alpha/Numeric | 2 | Mnemonic |
| Procedure | Alpha/Numeric | 5 | CPT, HCPCS |
| timeframe | Alpha/Numeric | 3 | Mnemonic for timeframe or total |
| 50th percentile | Numeric | 4 | Beginning percentile range |
| 50th percentile | Numeric | 4 | ending percentile range |
| 75th percentile | Numeric | 4 | beginning percentile range |
| 75th percentile | Numeric | 4 | ending percentile range |
| 95th percentile | Numeric | 4 | beginning percentile range |
| 95th percentile | Numeric | 4 | ending percentile range |
| Mode | Numeric | 3 | Numeric Count |
| Count | Numeric | 7 | Number of EOCs for timeframe |
| Sum | Numeric | 7 | Number of services for timeframe |
| Weighting | Numeric | 6 | Numeric count, assumed decimal (4.2) |
| Update | Character | 1 | A, C, or Blank |
| Total | | 63 | |

USE:
  This table shows which CPTs are historically billed and statistically how often for a Specific Index Code.

Category Parameter Table

This table contains a listing of the procedural categories identified for each index code listed chronologically with associated percentiles, mode, and average.

| | | | |
|---|---|---|---|
| Index Code | Alpha/Numeric | 5 | Left justified assumed decimal after 3rd position. |
| Profile | Alpha/Numeric | 2 | Mnemonic |
| Category | Alpha/Numeric | 4 | category |
| timeframe | Alpha/Numeric | 3 | Mnemonic for timeframe or total |
| 50th percentile | Numeric | 4 | beginning percentile range |
| 50th percentile | Numeric | 4 | ending percentile range |
| 75th percentile | Numeric | 4 | beginning percentile range |
| 75th percentile | Numeric | 4 | ending percentile range |
| 95th percentile | Numeric | 4 | beginning percentile range |
| 95th percentile | Numeric | 4 | and ending percentile range |
| Mode | Numeric | 3 | Numeric Count, assumed decimal (4.2) |
| Count | Numeric | 7 | Number of EOCs for the timeframe |
| Sum | Numeric | 7 | Number of services for the timeframe |
| Update | Character | 1 | A, C, or Blank |
| Total | | 56 | |

USE:

This table shows which Procedural Categories are historically billed and statistically how often for a Specific Index Code.

Duration Parameter Table

This table contains the EOC duration distribution for a given Index code.

| Index Code | Alpha/Numeric | 5 | Left justified assumed decimal after 3rd position. |
|---|---|---|---|
| Profile | Alpha/Numeric | 2 | Mnemonic |
| 50th percentile | Numeric | 4 | beginning range |
| 50th percentile | Numeric | 4 | ending range |
| 75th percentile | Numeric | 4 | beginning range |
| 75th percentile | Numeric | 4 | ending range |
| 95th percentile | Numeric | 4 | beginning range |
| 95th percentile | Numeric | 4 | ending range |
| Mode | Numeric | 3 | beginning and ending range |
| Update | Character | 2 | A = Add |
|  |  |  | C = Change |
| Total |  | 36 |  |

USE:

This table gives access to Statistical information about EOC durations of care for a given index code.

It interrelates with:
Index Detail table
Parameter table

Category Table

This Table provides a grouping of CPT codes into categories of similar services.

| Category | Alpha/Numeric | 4 | Mnemonics |
|---|---|---|---|
| Beg-CPT | Alpha/Numeric | 5 | Beginning CPT Range |
| End-CPT | Alpha/Numeric | 5 | Ending CPT Range |
| Update | Character | 1 | A, C, or Blank |
| Total |  | 15 |  |

USE:

Procedure codes have been categorized according to most likely type of service they may represent. It could be characterized as a sorting mechanism for procedure codes.

The mnemonic used for this category is as follows:

$E_1$=Major E and M $E_2$=Minor E and M $L_1$=Major Laboratory $L_2$=Minor Laboratory $R_{D1}$=Major Diagnostic Radiology $R_{D2}$=Minor Diagnostic Radiology $R_{T1}$=Major Therapeutic Radiology $R_{T2}$=Minor Therapeutic Radiology $O_1$=Major Oncology Radiology $O_2$=Minor Oncology Radiology $M_{D1}$=Major Diagnostic Medicine $M_{D2}$=Minor Diagnostic Medicine $M_{T1}$=Major Therapeutic Medicine $M_{T2}$=Minor Diagnostic Medicine $S_{D1}$=Major Diagnostic Surgery $S_{D2}$=Minor Diagnostic Surgery $S_{T1}$=Major Therapeutic Surgery $S_{T2}$=Minor Therapeutic Surgery $A_1$=Major Anesthesia $A_2$=Minor Anesthesia $P_1$=Pathology J=Adjunct Categories are also used for arraying Episodes of Care into profile classes or can be reported as an aggregate. The subsets of the aggregate are:

0 Common Profile
1 Surgery/Radiation/Medicine Profile
2 Medicine/Radiation Profile
3 Surgery/Radiation Profile
4 Surgery/Medicine Profile
5 Radiation Profile
6 Medicine Profile
7 Surgery Profile This table interrelates with:
Parameter Table
Qualifying Tables
Procedure Table Qualifying Master Table This table provides a preliminary step for determining qualifying circumstances that may eliminate a patient history for determination of an Episode of Care. It also provides the initial sort of an episode of care for a specific profile class.

| Index Code | Alpha/Numeric | 5 | Left justified, assumed decimal after 3rd position |
|---|---|---|---|
| Scope | Alpha | 1 | P = Patient |
|  |  |  | E = Episode of Care |
|  |  |  | B = Both |
| Profile | Alpha/Numeric | 2 | Mnemonic or Blank |
| Group | Alpha/Numeric | 5 | Correlates to group ID in Qualifying Group Table |
| Update | Character | 1 | A, C, or Blank |
| Total |  | 14 |  |

USE:

Preliminary step in EOC qualifying process.

This table interrelates with:
Index Detail Table
Qualifying Group Table

The Scope field of the Qualifying Master Table outlines which set of qualifying circumstances are to be applied. The values of the Scope field include P=patient level, E=Episode of Care level, or B=both.

The Profile field is numbered based on the 8 different profiles (also outlined under the category table. If blank, a profile is not relevant. They are as follows:

0. Common Profile
1. Surgery/Medicine/Radiation Profile
2. Medicine/Radiation Profile
3. Surgery/Radiation Profile
4. Surgery/Medicine Profile
5. Radiation Profile
6. Medicine Profile
7. Surgery Profile The Group field assigns a 5 byte mnemonic that establishes a set of qualifying rule sets for a given index code. This field keys directly to the Qualifying Group Table. The majority of the groups relate to profile classes.

Qualifying Group Table

This table groups certain qualifying circumstances to aid in an efficient search for data meeting the criteria.

| Group | Alpha/Numeric | 5 | Left justified assumed decimal after 3rd position |
|---|---|---|---|
| Rule Type | Alpha/Numeric | 2 | II = Index Code specific rule<br>IS = specific ICD code rule<br>IC = multiple ICD to category rule<br>CC = Multiple code rule<br>CS = code specific rule<br>IG = ICD to gender rule<br>IA = ICD to age rule |
| Logical | Alpha/Numeric | 1 | T = True F = False (toggle) |
| Rule Identifier | Alpha/Numeric | 1 | M = Male F = Female if IG rule type |
| Number required | numeric | 2 | number value |
| Update | Character | 1 | A, C, or Blank |
| Total | | 15 | |

USE:
This table groups all rules qualifying EOCs.
This table interrelates with:
Qualifying Index Table
Qualifying Code Table
Qualifying Master Table A rule type (or rule types) is assigned by group delineating if the rule applies to a single or multiple ICD, single or multiple CPT or category or any combination thereof.

The Rule Type is a mnemonic which assigns a common type of logic that is to be implemented in the search for the qualifying circumstances. It is possible that the same rule type could be associated with many different rule identifiers. The rule type will also point to either the Qualifying Index Table or the Qualifying Code Table.

The following is a listing of the rule types. (One skilled in the art would understand that additional rule types and associated programming logic may be implemented):

Rule Types associated with Qualifying Index Table:

II This related directly to the Index code only.

IC This rule is for any indicated ICD code associated with the Index code as it relates to a category or procedure.

IS This rule is for a specific indicated ICD code associated with the Index code as it relates to a category or procedure.

IG This rule is for any indicated ICD code associated with the Index code as it relates to age.

Rule Types associated with Qualifying Code Table:

CC This rule is for a specific procedure or category as it relates to another specific procedure or category for any ICD code associated with the Index code.

CS This is for a specific procedure or category as it relates to a specific ICD code associated with the Index code.

The rule identifier is an assigned mnemonic based on what the rule is to achieve.

The Logical indicates if the rule is positive or negative (inclusionary or exclusionary)

The Number Required is a count of the number of occurrences required for the rule to be valid.

Qualifying Index Table

Table houses qualifying circumstances based on presence or non-existence of Specific procedures and/or ICD codes that would qualify or disqualify a patient history in the determination of an Episode of Care.

| Rule Type | Alpha/Numeric | 2 | II = Index Code specific rule<br>IS = specific ICD code rule<br>IC = multiple ICD to category rule<br>IA = ICD to age rule<br>EG = ICD to gender |
|---|---|---|---|
| Rule Identifier | Alpha/Numeric | 4 | assigned from Qualifying Master Table |
| Indicator | Alpha/Numeric | 2 | I = Index code<br>R = Related<br>S = signs/symptoms<br>RO = Rule out<br>M = Miscoded<br>V = Vcodes<br>MI = Miscoded Index or Blank |
| Code | Alpha/Numeric | 5 | category, CPT, HCPCS, ICD or blank |
| Update | Character | 1 | A, C, or Blank |
| Total | | 14 | |

USE:
To act as a qualifying mechanism for determining if claims information can be used in the assignment of an EOC
This table interrelates with:
Procedure Table
Category Table
Qualifying Group Table
ICD Description Table
Index Detail Table

Qualifying Code Table

Table houses qualifying circumstances based on the presence or non-existence of a specific combination of procedure codes that would qualify or disqualify a patient history in the determination of an Episode of Care.

| Rule Type | Alpha/Numeric | 2 | CC = Multiple code rule<br>CS = code specific rule |
|---|---|---|---|
| Rule Identifier | Alpha/Numeric | 4 | As labeled in Qualifying Master Table |
| Primary code | Alpha/Numeric | 5 | CPT, HCPCS or category or ICD |
| Secondary Code | Alpha/Numeric | 5 | CPT, HCPCS or category or ICD |
| Update | Character | 1 | A, C, or Blank |
| Total | | 14 | |

USE:
To act as a qualifying mechanism for determining if claims information can be used in the assignment of an EOC.
This table interrelates with:
Procedure Table
Category Table
Qualifying Group Table

Specialty Table

Table provides a listing of medical specialties with an assigned numeric identifier.

| | | | |
|---|---|---|---|
| Specialty (Key) | Alpha/Numeric | 3 | Medicare specialty indicator |
| Beg-CPT | Alpha/Numeric | 5 | Beginning CPT to include |
| End-CPT | Alpha/Numeric | 5 | Ending CPT to include |
| Update | Character | 1 | A, C, or Blank |
| Total | | 14 | |

USE:

This table is used to specify which Specialty is most commonly used with which CPT.

A description of the specialty will be in the documentation.

Zip/Region Table

Table provides a listing of geographical zip codes sorted into 10 regional zones, standard HCFA information.

| | | | |
|---|---|---|---|
| Region Indicator | Alpha/Numeric | 2 | Medicares Ten Regions |
| Beg-Zip Code | Numeric | 5 | Beginning Zip Code Range |
| Beg-Zip Code | Numeric | 5 | Ending Zip Code Range |
| Update | Character | 1 | A, C, or Blank |
| Total | | 13 | |

USE:

This table is used to specify which Medicare Region to use for the statistic table.

Specialty Statistic Table

Table provides a listing of medical specialties with an assigned numeric identifier.

| | | | |
|---|---|---|---|
| Index Code | Alpha/Numeric | 5 | Left justified assumed decimal after 3rd position. |
| Specialty | Alpha/Numeric | 3 | |
| Beg-CPT Code | Alpha/Numeric | 5 | Beginning Range (Service Area) |
| Beg-CPT Code | Alpha/Numeric | 5 | Ending Range (Service Area) |
| Category | Alpha/Numeric | 4 | Mnemonic |
| Multiplier | Numeric | 6 | Implied decimal (4.2) |
| Update | Character | 1 | A, C, or Blank |
| Total | | 29 | |

USE:

This table is a matrix that is directly tied to the parameter table by the index code. Its purpose is to give a numeric multiplier that is applied to the occurrence field in the parameter table, to vary the parameter by service area and/or sex and/or region. (i.e., if the occurrence is 2 and the multiplier for a specialist is 1.5, the specialist may receive a total of 3.) Multiple multipliers may be applicable to each parameter.

Age/Gender Statistic Table

Table provides a listing of each CPT code for an index code with a numerical factor used to adjust the frequency of each code by age and/or gender specific data analysis.

| | | | |
|---|---|---|---|
| Index Code | Alpha/Numeric | 5 | Left justified assumed decimal after 3rd position. |
| Age | Alpha/Numeric | 2 | 00–99 |
| Sex | Alpha/Numeric | 1 | M, F or Blank |
| Category | Alpha/Numeric | 3 | Mnemonic |
| Multiplier | Decimal | 6 | Implied decimal (4.2) |
| Update | Character | 1 | A, C, or Blank |
| Total | | 18 | |

USE:

This table is a matrix that is directly tied to the parameter table by the index code. Its purpose is to give a numeric multiplier that is applied to the occurrence field in the parameter table, to vary the parameter by service area and/or sex and/or region. (i.e. if the occurrence is 2 and the multiplier for a male is 1.5, the male may receive a total of 3.) Multiple multipliers may be applicable to each parameter.

Region Statistic Table

Table provides a listing of CPT codes for an index code with a numerical factor used to adjust the frequency of each code by regional data analysis.

| | | | |
|---|---|---|---|
| Index Code | Alpha/Numeric | 5 | Left justified assumed decimal after 3rd position. |
| Region | Alpha/Numeric | 2 | Medicares Ten Regions |
| Multiplier | Decimal | 6 | Implied decimal (4.2) |
| Update | Character | 1 | A, C, or Blank |
| Total | | 14 | |

USE:

This table is a matrix that is directly tied to the parameter table by the index code. Its purpose is to give a numeric multiplier that is applied to the occurrence field in the parameter table, to vary the parameter by service area and/or sex and/or region. (i.e., if the occurrence is 2 and the multiplier for a region is 1.5, the region may receive a total of 3.) Multiple multipliers may be applicable to each parameter.

File Layout for Claims Data Contribution

We prefer Electronic Media Claims National Standard Format; however, if you are not using EMC the following is our suggested layout. Please include an exact layout of the format you use with your submission. The record layout that follows is for each line item that appears on a claim. The charge (field 19) should be the non-discounted fee-for-service. There should be no aggregation or fragmentation.

| Field Number | Description | Length | Alpha/Numeric | Comments |
|---|---|---|---|---|
| 1. | Rendering Provider ID | 15 | A/N | Unique provider identification number or SSN |
| 2. | Billing Provider ID | 15 | A/N | Unique provider identification number or SSN |
| 3. | Provider Specialty | 3 | A/N | Supply a List of Specialty codes used |
| 4. | Patient ID | 17 | A/N | Unique patient ID number or SSN. May be an encrypted or encoded format. |
| 5. | DOB | 6 | N | Patient Date of Birth MMDDYY |
| 6. | Sex | 1 | A | M = Male, F = Female |
| 7. | Subscriber ID | 25 | A/N | Insured's I.D. No., Normally SSN |
| 8. | Relationship | 1 | N | Patient to Subscriber, 1 = Self, 2 = Spouse, 3 = Dependent |
| 9. | Bill ID | 15 | A/N | Unique claim/bill identification number |
| 10. | From Date of Service | 6 | N | MMDDYY |
| 11. | To Date of Service | 6 | N | MMDDYY |
| 12. | Provider Zip | 5 | N | Standard 5 digit Zip Code |
| 13. | Place of Service | 2 | A/N | Supply a list of POS codes used |
| 14. | Type of Service | 2 | A/N | Supply a list of TOS codes used |
| 15. | Procedure Code | 5 | N | Submitted CPT or HCPC code |
| 16. | Modifier | 2 | N | Submitted CPT modifier |
| 17. | 2nd Modifier | 2 | N | If multiple modifiers are submitted, show the second modifier used. Anesthesia Modifiers (P1–P6) |
| 18. | Claim type | 3 | A/N | Payor Class Code-W/C, HCFA, Medicaid etc. |
| 19. | Charge | 5 | N | Billed amount, right justified, whole dollars |
| 20. | Allowed Amount | 5 | N | Right justified, whole dollars |
| 21. | # of days/units | 5 | N | number of days and/or units |
| 22. | Anesthesia time | 3 | N | Actual Minutes |
| 23. | ICD1 | 5 | A/N | First diagnostic code attached to procedure |
| 24. | ICD2 | 5 | A/N | Second diagnostic code attached to procedure (Both ICD1 & ICD2 are left justified, assumed decimal after 3rd byte) |
| 25. | ICD3 | 5 | A/N | Third diagnostic code attached to procedure |
| 26. | ICD4 | 5 | A/N | Fourth diagnostic code attached to procedure |
| 27. | Out-patient facility | 5 | A/N | Outpatient facility/outpatient hospital identifier |
| 28. | Revenue Code | 3 | N | Revenue center code |

Acceptable Media Types 9 track tape: 1600 or 6250 BPI, ASCII or EBCDIC, Labeled or Unlabeled, Unpacked data, Fixed record lengths Floppy disk; 3.5" (1.44 Mb or 720K) or 5.25" (1.2 Mb or 360K), Standard MS-DOS formatted disk, ASCII fixed record length or delimited file DC 600A or DC 6150 cartridge : "TAR" or single ASCII or EBCDIC file, Unpacked data, Fixed record lengths 8 mm Exabyte tape: "TAR" or single ASCII or EBCDIC file, Unpacked data, Fixed record lengths 3480 cartridge: Unpacked data, Fixed record lengths, Compressed or Uncompressed Maximum Block size 64,280

Data Processing Methodology

This invention is a process for analyzing healthcare providers' billing patterns to assess utilization patterns of medical services. The method of the invention incorporates a set of statistically derived and clinically validated episode of care data to be used as a paradigm for analyzing and comparing providers' services for specific diagnoses or medical conditions. This invention utilizes a series of processes to analyze the client's healthcare claims history to create unique parameters. In its preferred embodiment, the invention is implemented in software. The invention provides the following functions or tools to the client: creation of local profiles, display of profiles and comparison of profiles.

The creation of local profiles function gives the client the ability to develop unique episode of care profiles utilizing their own claims history data. The process for creating these profiles is identical to the process used in the development of the reference profiles.

The display of profiles function provides a look-up capability for information stored in the reference tables or in client generated profile tables. This look-up capability may be displayed on the computer screen or viewed as a hardcopy printout.

The comparison of profiles function provides a comparison between any two profile sources with attention to variance between them. Some examples include comparing client specific profiles to reference tables, comparing a specific subset of the client's data (eg, single provider) against either reference tables or the client's profiles, or comparing different subsets of the client's profiles to subsets of reference tables.

Figure 10:
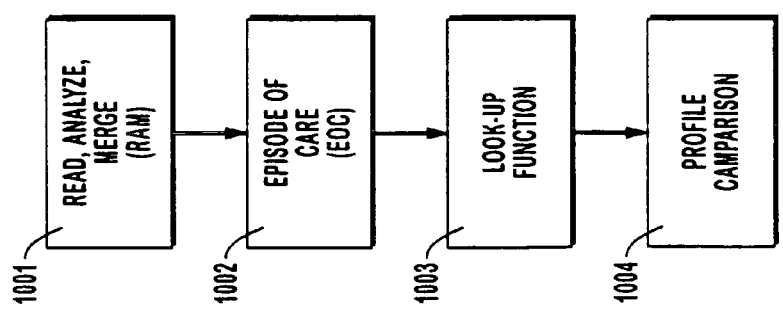
FIG. 10 depicts principle elements of the invention and their relationship to each other.

There are four main processes involved in the invention, as depicted in FIG. 10. These are Read, Analyze and Merge (RAM), 1001, further depicted in FIG. 11; Episode of Care analysis (EOC), 1002, further depicted in FIG. 12; Look-up function, 1003, further depicted in FIGS. 13 and 14; and Profile Comparison, 1004, further depicted in FIG. 15. The invention also includes an innovative reporting mechanism. Each of these four main processes and the reporting mechanism is described in detail in the remainder of this section.

A. Transforming Raw Data Into an Informative Database

Both the RAM and the EOC processes involve healthcare claims history search and analysis. The intent of the RAM and the EOC claims history processing is to enable the end user to establish their own unique profiles based on their existing claims data information. Developing a database of historical provider billing data which will be used to provide the functionality of the invention is the first step in the invention.

1. Read, Analyze and Merge ("RAM")

In order to define a profile a significant quantity of historical medical provider billing information must be analyzed. As indicated above, the provider billings may come from a variety of sources, with the general guideline that accuracy and completeness of the data and a statistically significant sample of provider billings are required to develop a reliable profile. In the preferred embodiment of the invention, no less than two years of consecutive claims history are used to develop the profiles. The RAM process verifies existence and validity of all data elements in a claims history before the data is processed to develop a profile. The reader is directed to FIGS. 1 and 6–8 for pictorial representations of the preferred embodiment of the invention. FIG. 1 depicts the high level steps performed in one embodiment of the invention. The data flow shown in FIG. 1 includes loading client data 101 from tape 100, reordering various fields 103 and performing date of service expansion 104 as necessary. Next, data are merged (combined) 1–5 and sorted 106 to ensure all bill IDs are grouped together. The data 108 are then read, analyzed and merged into an extended data set (EDS) 110. Reporting and any other processing may occur 111 and an Episode of Care database 112 is created. In the preferred embodiment of the invention, the steps of the invention are implemented in a software product referred to as Care Trends available from Medicode, Inc. of Salt Lake City, Utah.

Figure 6:
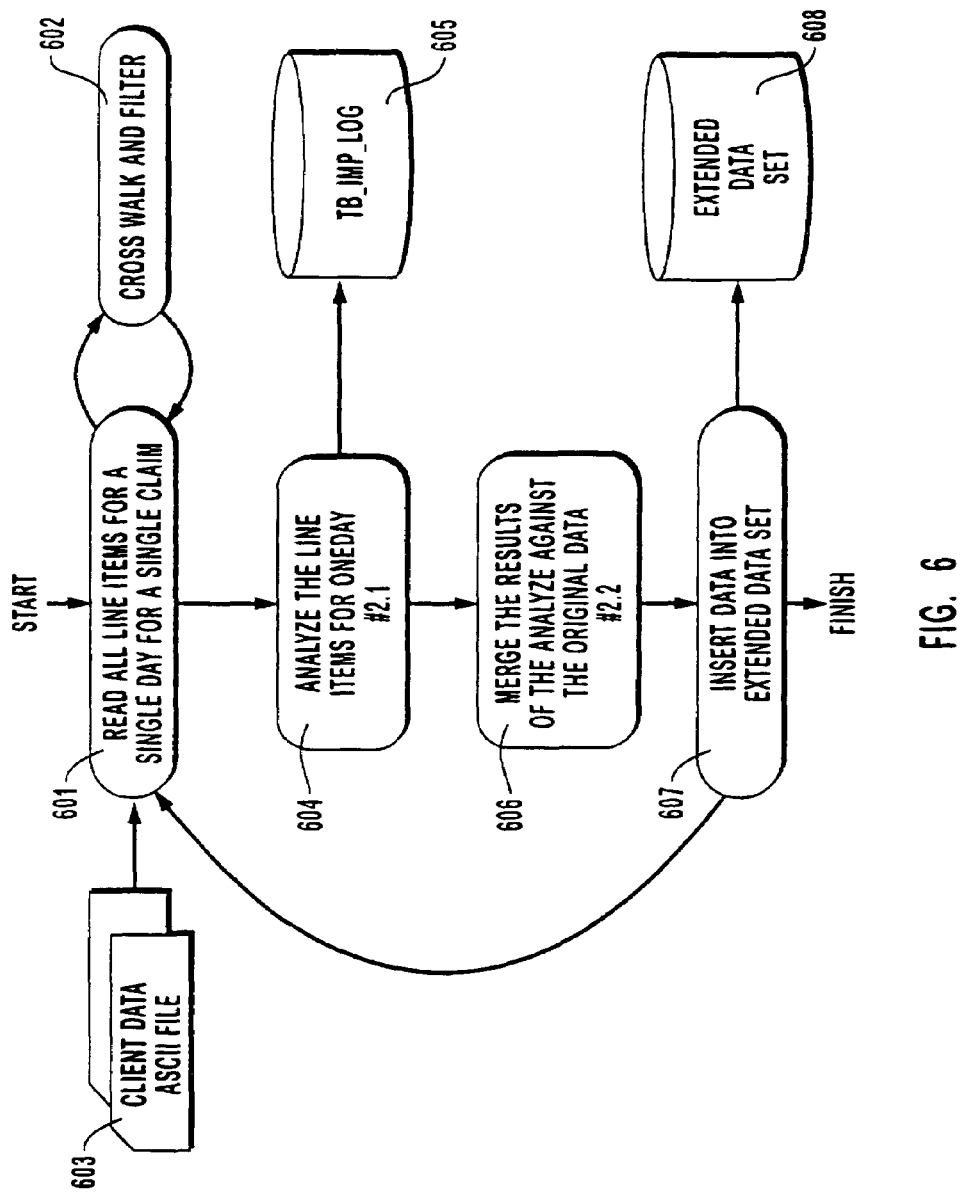
FIGS. 6–8 depicts processing of data before episode of care processing begins.

FIG. 6 depicts read, analyze and merge processing that occurs in the preferred embodiment of the invention. First, one claim at a time the data 603 are read 601, crosswalked and scrubbed (filtered) 602. Then a claim is analyzed 604 with the results output to a log file 605. The results in the log file 605 are then compared 606 to the original claim data and inserted 607 into an extended data set 608.

Figure 7:
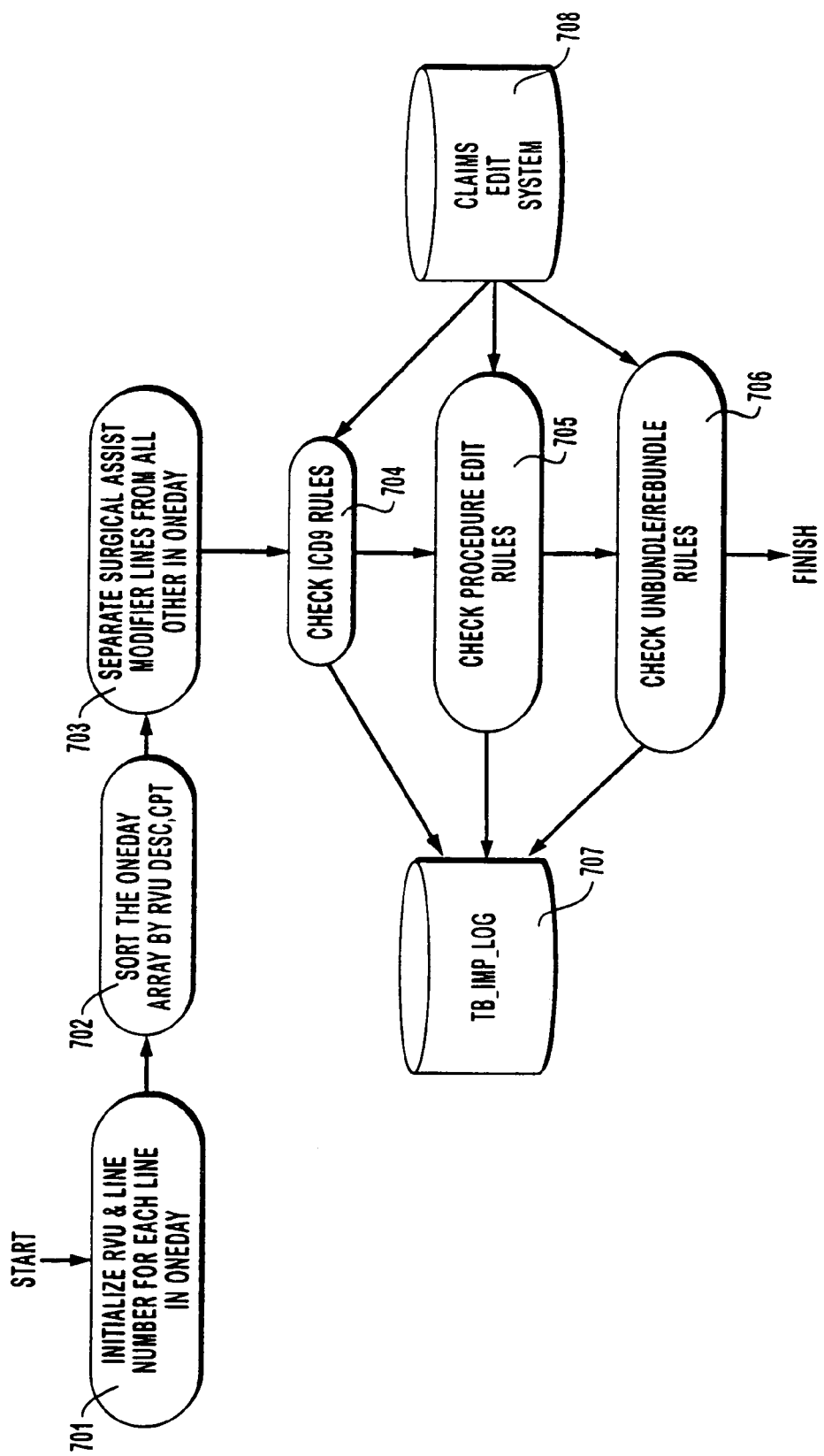

FIG. 7 depicts an analytical process of the preferred embodiment that includes initializing 701 RVU and line number for each line of the claim and sorting 702 by RVU (descending) and CPT and charge in order to prepare for proper analysis by Medicode's Claims Edit System (CES). Then 703 line items are split into two groupings of surgical assistant modifiers and all other modifiers in separate groups. Each of the two groups is then validated 704 against disease classification codes (ICD 9); procedure edits rules 705 (CES tables) and unbundle/rebundle edits 706 are performed.

Figure 8:
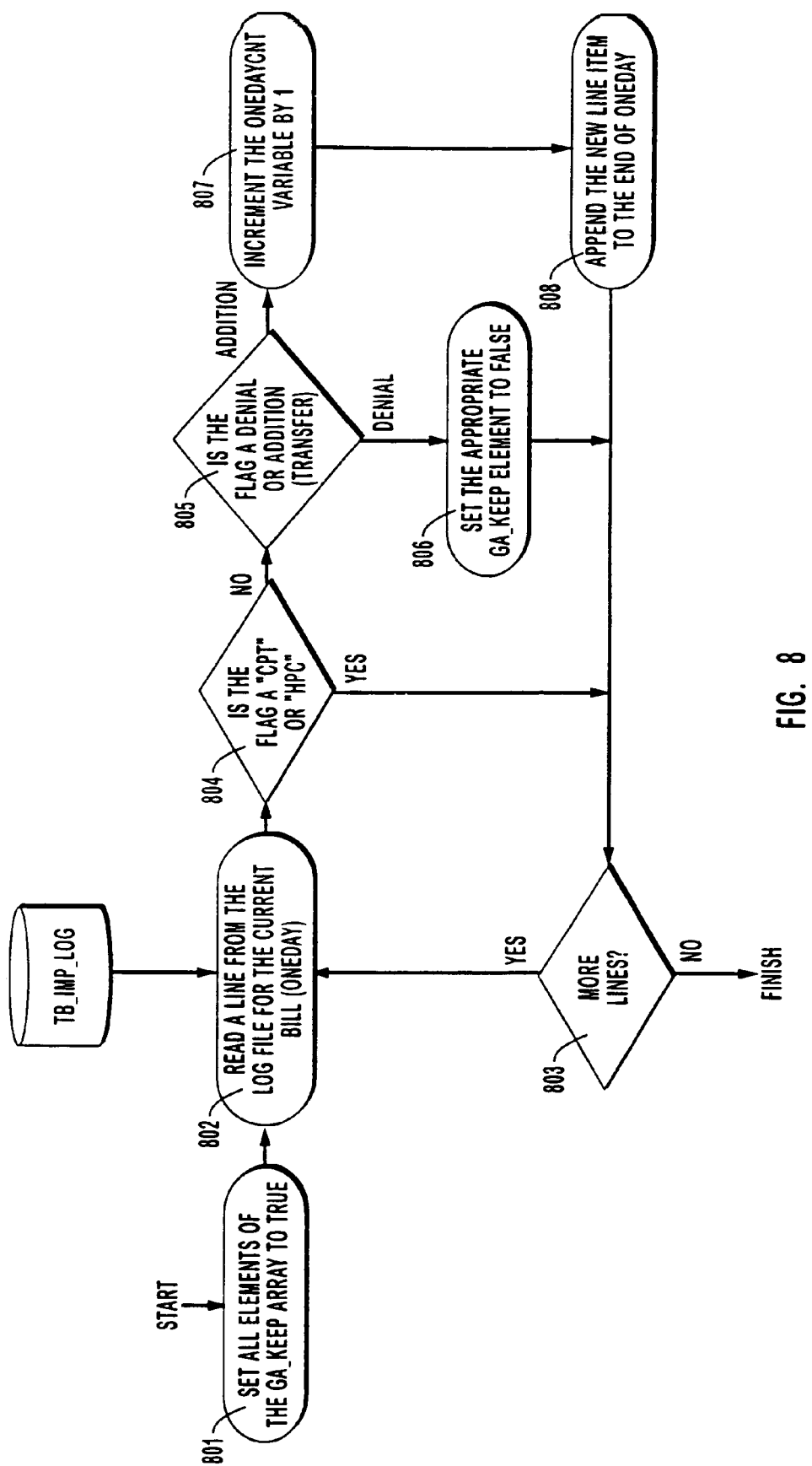

FIG. 8 depicts the merge process of the preferred embodiment of the invention. It includes reading 802 each line from the log file for the current bill, proceeding with processing if the record read is pertinent 804 and determining whether to add the record to the extended data set 805–807.

Figure 11:
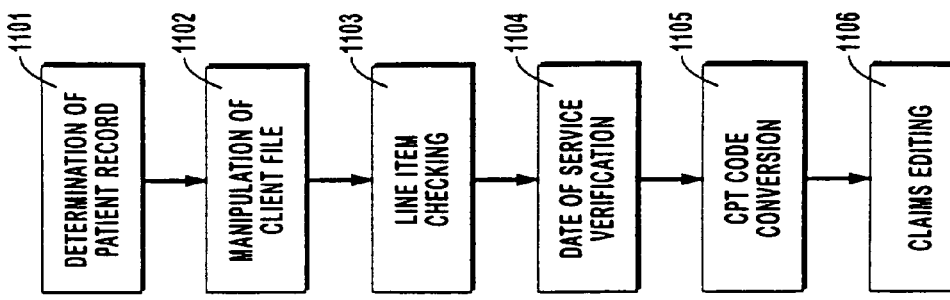
FIG. 11 depicts the process of the preferred embodiment of the Read, Analyze, Merge element of the invention.

The following text includes a written description of the RAM processing that is performed in the preferred embodiment of the invention. FIG. 11 shows the RAM process.

The first step in the RAM process is determination of a patient record, 1101. It is necessary to establish a patient record that can be used in the episode of care extraction process (explained in detail below). In the preferred embodiment, a patient record is identified as a unique patient history involving no less than two years of sequential claims history. Because identifying patient information is often removed from patient records to ensure patient confidentiality, patient information such as subscriber/relationship, patient ID, age, gender, bill ID and claim ID may be useful in positively identifying a particular patient. It should be noted that claims history data from various sources may need to be handled differently to identify patient records due to differences in file organization and level of detail of information provided. The amount of information desired to be captured may vary in different embodiments of the invention, but generally the information to be captured is that on a standard HCFA 1500 billing form, Electronic Media Claims, UB 82 or UB 92 claim forms, all of which are generally known in the industry.

The next step, 1102, is the manipulation of the client file layout to extrapolate or crosswalk the pertinent information in order to conform to the logic of the invention. Examples of this step include: translation of type of service, specialty type, modifiers, and/or place of service information.

The next steps involve the validation of claims elements. Each line item of claims history is compared against the Procedure, Description tables, (such as CPT or HCPCS description tables; such tables generally are referred to as Description Tables and may contain any coding schemes) and the ICD description tables to validate the codes contained in the line item, 1103. Line items with an invalid code are not included in the remainder of RAM processing, though they are counted for future reference. Line items which indicate services being performed over a period of more than one day are expanded into numerous line items, one for each service performed, 1104. The services are then each given a unique date of service beginning with the "date of service from" for the first line item and ending with the "date of service to" for the last line item. The last validation step, 1105, is the conversion of old CPT codes to new CPT codes. This step is essential to provide the most accurate statistics relative to physician office and hospital visits (termed Evaluation and Management Services).

The last step of the RAM process is to edit all claims for errors, through an appropriate claims edit tool, 1106. In the preferred embodiment, software known as "CLAIMS EDIT SYSTEM" which is available from Medicode, Inc. located in Salt Lake City, Utah is used to detect and correct any duplicate line items or inappropriately billed services. This results in an appropriately processed set of raw data that is now in a condition for episode of care processing. The reader is directed to the RAM source code in the Microfiche Appendix for all details of this processing performed in the preferred embodiment.

Figure 9:
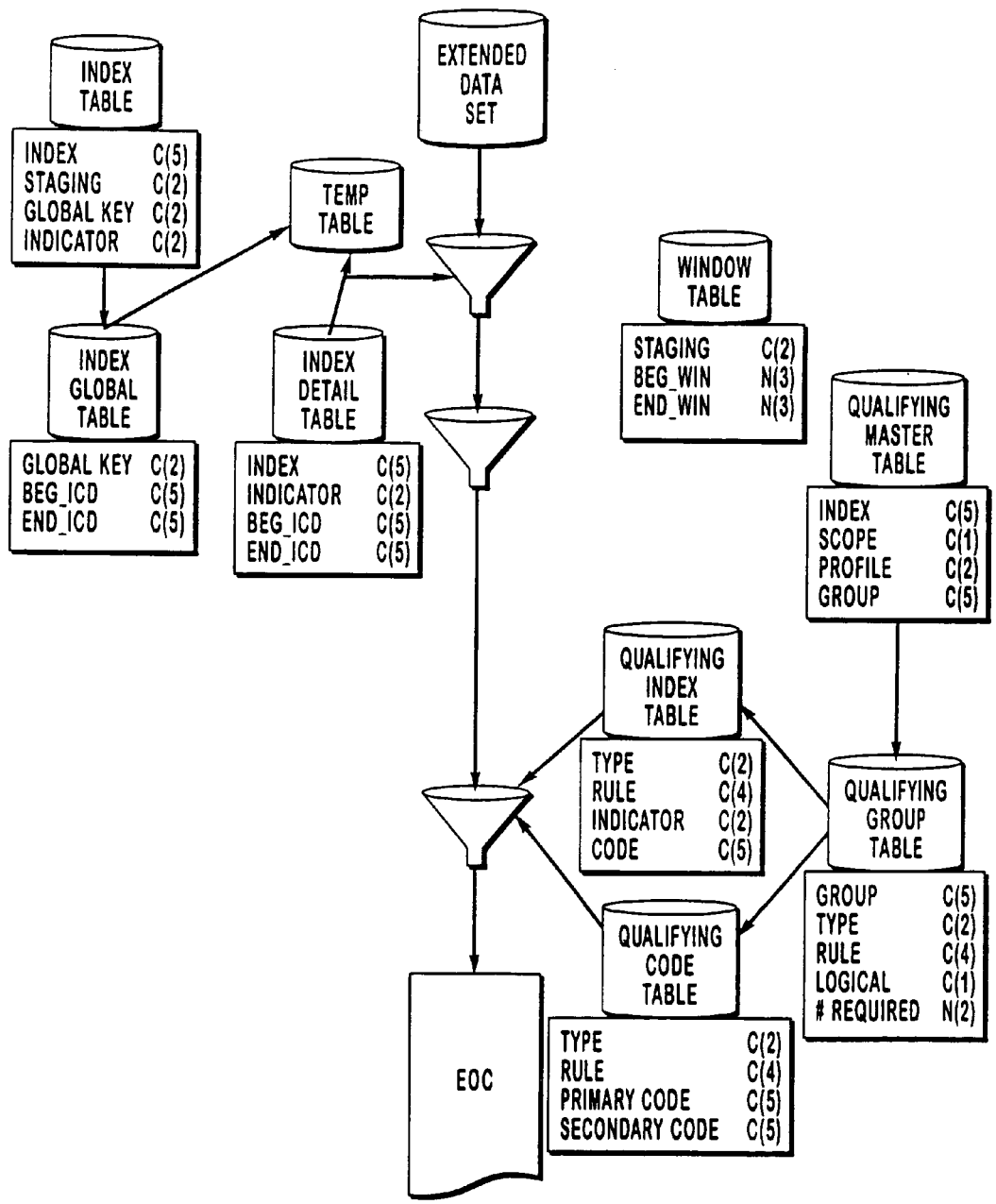
FIG. 9 depicts episode of care processing.

FIG. 9 depicts episode of care formation in the preferred embodiment. This processing includes processing the records in the extended data set that relate to the current index code. This relation is determined by the index tables. Then the records are broken into potential episodes of care based on a period of time specified in a window table. Then the episode of care is qualified based on the rules in a qualifying table. Qualifying episodes of care are inserted into the episode of care table.

2. Determination of Episode of Care

Figure 2:
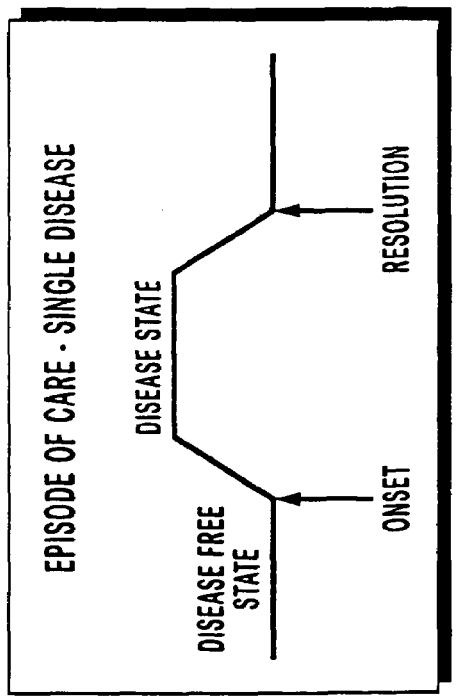
FIG. 2 depicts an episode of care for a single disease.

The next step in transforming raw data into a useful database is to determine episodes of care for the data that has already undergone RAM processing. In the invention, a database is created which contains profiles for various diagnoses, chronic and otherwise, including complications indicators. Creation of the database depends on accurately defining an episode of care ("EOC") for each diagnosis. An episode of care is generally considered to be all healthcare services provided to a patient for the diagnosis, treatment, and aftercare of a specific medical condition. The episode of care for a single disease is depicted in FIG. 2. In the simplicity of the figure, it can be seen that for the diagnosis in question, all healthcare services provided between onset and resolution should be incorporated into the database. An example of this would be a patient who has been afflicted with acute appendicitis. The patient's life prior to onset of the acute appendicitis would be considered a disease free state. On some date, the patient would notice symptoms of acute appendicitis (although he may not know the diagnosis) that cause him to seek the attention of a medical provider. That event would be considered the onset. During the disease state, numerous events may occur, such as the patient consulting a family practitioner, consulting a surgeon, laboratory work and surgical services being performed, and follow-up visits with the provider(s). When further follow-up is no longer required, resolution has been reached. Thus an episode of care has been defined and data from that patient's episode of care is used in the invention to construct a profile for the diagnosis applicable to that patient. Without the use of additional logic, however, the use of that definition of an episode of care would result in erroneous data being entered into the EOC database.

Figure 3:
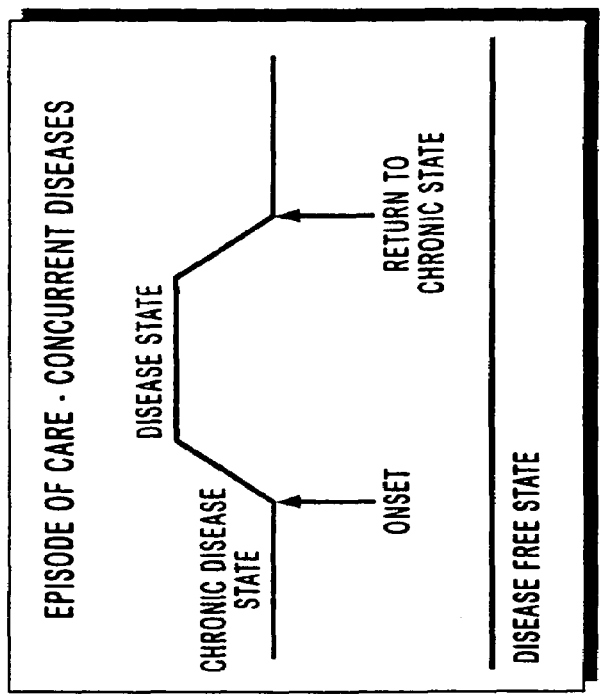
FIG. 3 depicts an episode of care for concurrent diseases.

For example, in FIG. 3 it can be seen that a patient suffering from a chronic disease who contracts a second disease could be treated both for the chronic disease and for the second disease during the disease state (i.e. between onset and resolution). If all medical provider billing data during the disease state were entered into the database, then the database would contain erroneous historical data for that individual's diagnosis. For example, if a patient who suffers from psoriasis were to be diagnosed with acute appendicitis and received treatment for psoriasis between the time of onset and resolution of his acute appendicitis, then the provider billings would contain both billings for treatment of the psoriasis and the acute appendicitis. Therefore the invention incorporates methods for discerning medical provider billings relevant to a particular diagnosis. Further, the disease state could be the active state of a chronic disease, and resolution could be the disease returning to its inactive state. A method for handling this situation is therefore also provided.

Figure 4:
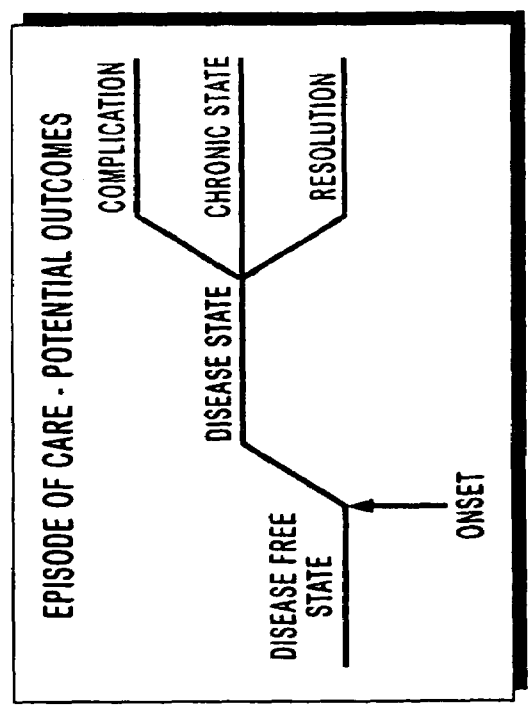
FIG. 4 depicts potential outcomes for an episode of care.

Other alternatives in the course of a disease further complicate accurately defining an episode of care. From FIG. 4 it can be seen that for any particular diagnosis, the outcome could be resolution, as described above, return to the chronic state of a disease, or complication of the disease. For example, if a patient has undergone an appendectomy, the patient may contract an infection following the surgical procedure. Because complications of various types and durations and in varying frequencies are associated with various diagnoses, a method for incorporating the complication data into the statistically-derived practice parameter is intended to be provided in the invention.

Figure 5:
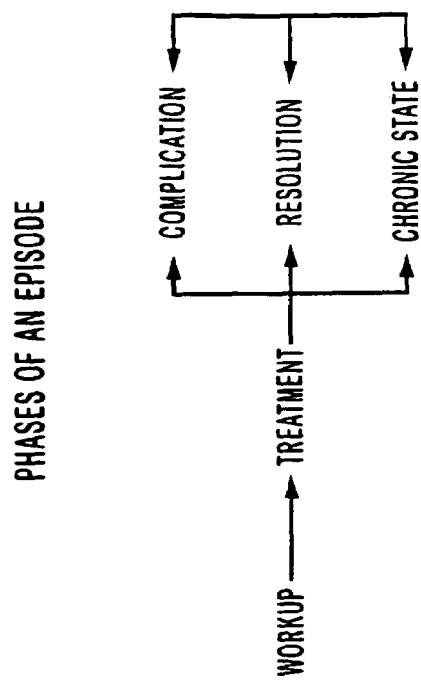
FIG. 5 depicts phases of an episode of care.

FIG. 5 depicts the phases of an episode of care, including the sequence of patient workup, treatment, and eventual solution, return to the chronic state, or complication followed by either resolution or return to the chronic state.

The method for defining an entire episode of care provided in the invention is used to construct a database of EOCs based on billing data that has been filtered to eliminate data irrelevant to the diagnosis which would lead to an erroneous profile. Essential to the determination of an EOC are certain qualifying circumstances. These circumstances are managed through the use of interrelational qualifying tables, to provide a mechanism for sorting patient history for the occurrence of specific procedures or ICD codes that are requisite for an EOC to be valid.

Figure 12:
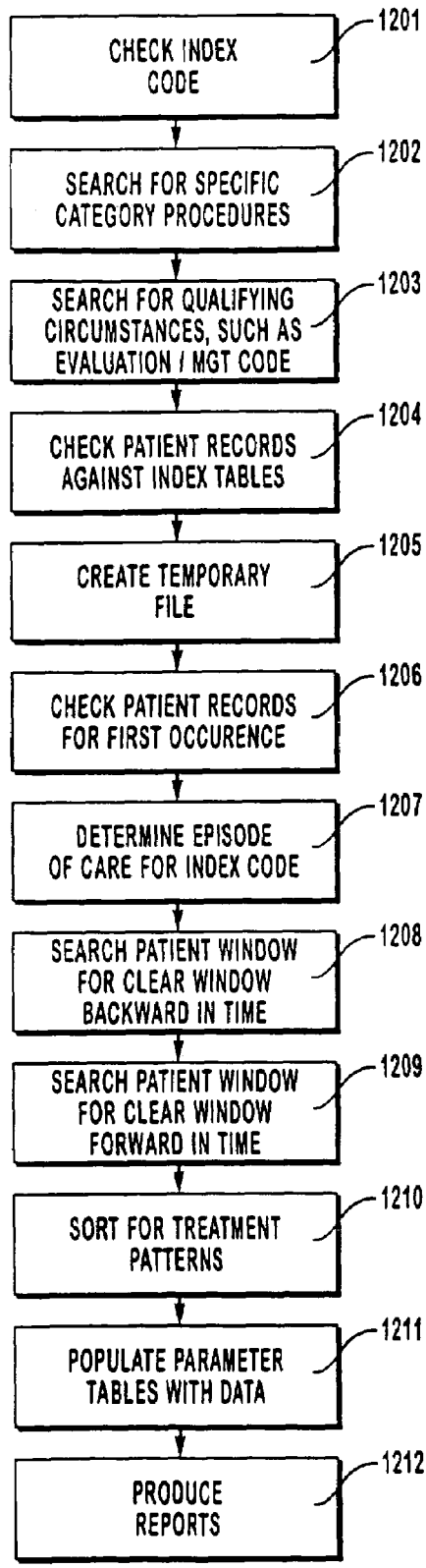
FIG. 12 depicts the process of the preferred embodiment of the Episode of Care element of the invention.

The steps used in the preferred embodiment to determine an episode of care are shown in FIG. 12 and as follows.

a.) Data Sort by Index Code

First, 1201, a temporary file is created based on combining the authorized and/or disallowed ICD codes that are associated with a given index code in the Index Global Table (listing preventative and aftercare codes) and the Index Detail tables. The temporary file is created using the Index Table, which determines whether or not the Index Detail Table only should be accessed or whether the Index Global Table is also necessary for drafting the temporary file. Second 1202, the raw data set which has undergone RAM processing is sorted by index code (i.e. general diagnosis) to find all patient records within a patient history having an occurrence of a particular index code. It is contemplated that the number of occurrences of a particular index code can be defined by the user. In the present embodiment, it is recommended that the particular index code being sought occur on at least two different dates of service. The valid components of these patient records are then checked against the interrelational qualifying tables to identify ICD codes associated with the chosen index code. The qualifying circumstances identify criteria such as procedures relating to specific medical conditions which may have been indicated as usually requiring an Evaluation and Management (E/M) service during the course of treatment. For example, an occurrence of a qualifying circumstance such as an E/M service during the patient history is considered in the criteria of an episode of care. In addition, the patient records are searched for any complicating ICD codes that would disqualify the patient record for inclusion in the EOC (such as diabetes or renal failure).

Fourth, 1203 the patient records are compared against the interrelational qualifying tables to ensure compliance with all patient-level qualifying rules. Patient records that fail to qualify are no longer considered for EOC evaluation for this Index Code, however, they may still qualify for other Index Code analysis. Fifth, 1205 all relevant line items for every remaining patient record are checked against the temporary file created in step one for complicating diagnosis codes. Any patient record thus identified with a complicating diagnosis code is removed from further EOC processing.

b.) Determination of Clear Windows

Clear window processing defines the onset and resolution points of an episode of care. The actual parameters used in clear window processing may vary in various implementations of the invention. A clear window time period is selected for the specific Index Code from the window table 1206. Next, 1207 proceeding chronologically, each record is compared with the record immediately preceding it. The first record read defines the beginning event of an initial episode of care and the last record read defines the terminating event of a final episode of care. If the two records being compared are separated by a time period equal to, or greater than, the clear window the earlier record is identified as the terminating event of the earlier episode and the later record is identified as the beginning event of the next episode. Accordingly, the initial episode of care and the final episode may be the same episode of care. It is also possible, for the first record and the last record to be the same record. This iterative process is continued for all remaining records for all patient claims. In this fashion potential EOCs are identified within the patient claims.

c.) Valid Episode of Care

Each potential episode is then checked to determine if the index code in question appears on the required number of dates of service within the EOC 1208. If the index code does not appear the required number of times, the potential EOC is pended. The qualifying tables are then checked to determine if the potential EOC meets the minimum criteria for procedure codes (such as surgical services) that are expected to be found within a potential episode of care for a given index code. If the minimum criteria are not found in an episode of care, it will not be considered in the profile summary. Processing continues for all patient records. Once an EOC has been determined for a set of claims history meeting the criteria for an Index code, a profile is assigned to the EOC based upon different combinations of treatment patterns that are likely to arise for a given medical condition, 1209. There are eight basic profile classes which outline the common combinations of treatment patterns to statistically analyze and store. These Profile Classes are:

0. Common Profile (diagnostic and E/M services common to all of the above).
1. Surgery/Medicine/Radiation Profile
2. Medicine/Radiation Profile
3. Surgery/Radiation Profile
4. Surgery/Medicine Profile
5. Radiation Profile
6. Medicine Profile
7. Surgery Profile
8. Summary Profile (summary of 0–7 above)

After all valid EOCs have been assigned to a unique profile processing continues with population of the procedure and category tables.

d.) Populating the Procedure and Category Parameter Tables

The data from qualified EOCs will be added to the procedure and category parameter tables 1210. Data from all of the episodes of care for each index code are inserted into the parameter tables to create the summary statistical profiles. In the preferred embodiment these tables are accessed by index code and populated with data from all the episodes of care for each index code to create and provide summary statistics. The procedure description table and category table are also accessed to determine a description of the procedure codes and the service category in which they fall.

The final step of the EOC process is the generation of output reports, 1211. The output report of this step can be either an online look-up report or a hard copy report. Reports are further described below.

The reader is directed to the Microfiche Appendix containing the source code for EOC processing and to FIG. 9 for supplementary information.

B. Use of the Database

1. Look-Up Function

In the preferred embodiment of the invention, a look-up function is provided so that various information available in the database may be accessed. In general, a specific diagnosis may be reviewed in each of the tables of the database based on ICD code. In various embodiments of the invention, other look-up functions may be provided based on nearly any category of information contained in the database. In the preferred embodiment of the invention display of profiles is performed as part of the look-up function. Information in the procedure and category parameter tables are displayed by index code sorted chronologically to show a profile.

Figure 13:
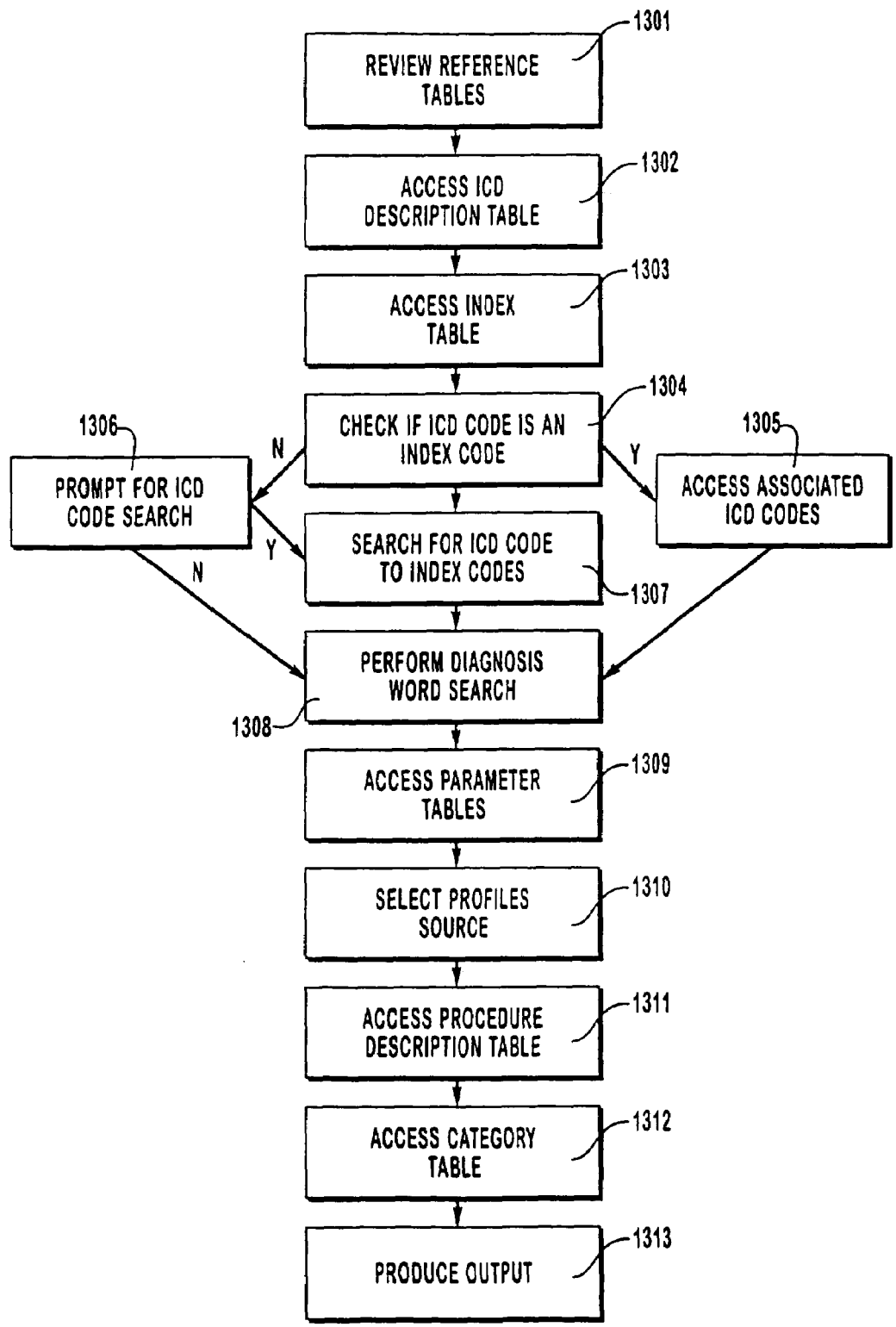
FIG. 13 depicts the process of the preferred embodiment of the Look-up element of the invention.

The specific steps of the preferred embodiment of the Look-Up function of the invention are shown in FIG. 13 and described as follows.

The first step, 1301, is to review the reference tables for a given Index ICD code. Once a specific diagnosis is chosen for review the process moves to step two. In step two, 1302, the ICD description table is accessed to verify that the ICD-9 code is valid, complete and to provide a description of the diagnosis. It will also indicate a risk adjustment factor assigned to the diagnosis.

In step three, the Index tables are accessed, 1303. Next, step four, 1304, is to determine whether or not the chosen ICD code is an Index code. If it is found as an Index code, any additional ICD codes associated which the selected Index code will be accessed, 1305. If a chosen diagnosis is not listed as an index code, a prompt, 1306, will allow a search for the selected ICD code to list which index code(s) it may be associated with and its indicator, 1307. A word search capability, 1308, is included in the look-up function applicable to the Index code display. A word or words of a diagnosis is entered and a search of possible ICD codes choices would be listed.

The next step, 1309, is to access the Parameter Tables to display selected profiles. The information provided is driven by the index code and is sorted chronologically, by profile class and by category of procedures. The user is then given the opportunity to choose whether the profiles to be accessed are from the reference tables, client developed profiles, or both, 1310. Next the Procedure Description Table, 1311, and the Category Table, 1312, are accessed to ascertain description of procedure codes and categories under which they fall.

The last step of the Look-Up function is the output of report product, 1313. This report may either be on-line look-up process or in the hard copy report format.

The preferred embodiment of the invention also performs subset profile look-up. This permits analysis of profiles based on selected subsets of data such as age, gender, region and provider specialty.

Figure 14:
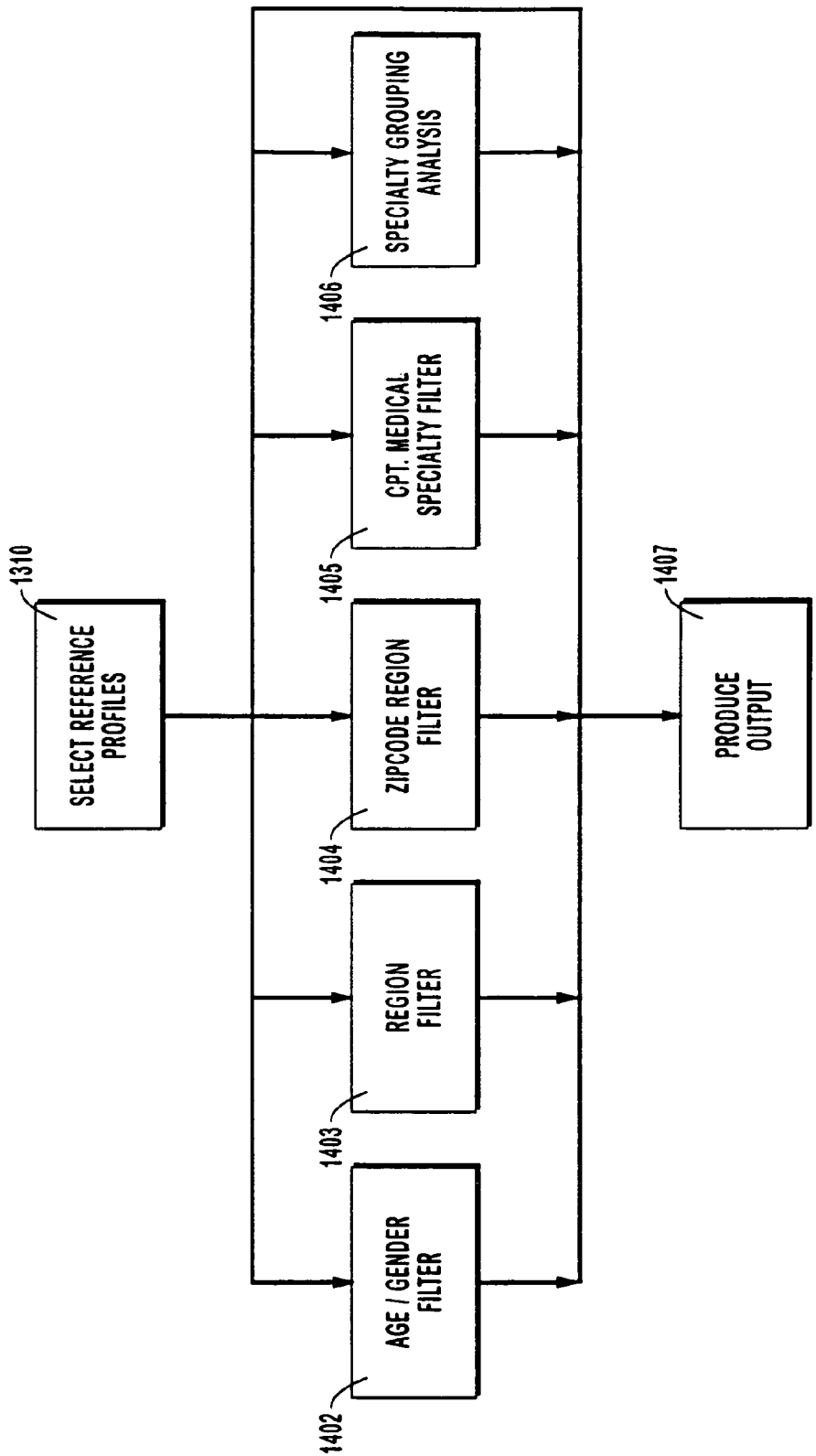
FIG. 14 depicts the process of the preferred embodiment of the Subset Parameter Look-up component of the Look-up element of the invention.

The process for the subset of profiles look-up includes all of the steps necessary for the general profiles look-up and includes the following additional steps shown in FIG. 14 and described below.

The Age/Gender Table is accessed to ascertain the standard age ranges and/or gender selection for a given profile, 1402. This information is stored by index code with an adjustment factor to be multiplied against the occurrence count of each procedure stored in the parameter table. For example, an adjustment factor of 0.6 associated with an age range of 0 to 17 would be calculated against an occurrence count of 10 for CPT code 71021 for Index code 493XX giving an age adjusted occurrence of 6 for that age range.

The Region Statistic Table, 1403, is accessed and used in a similar manner as the Age/Gender Table. This table has adjustment factors based on ten regions throughout the United States.

The Zip/Region Table, 1404, is accessed to identify what region a particular geographic zip code falls within.

The CPT Statistic Table, 1405, is accessed and used in a similar manner as the Age/Gender table. This table has adjustment factors based on different medical specialty groupings.

The Specialty table, 1406, is accessed to ascertain what particular specialty groupings are suggested.

The subset parameter Look-Up function also includes the capability of producing output reports, 1407. These reports can be on-line look-up process reports or hard-copy report format reports.

2. Comparison Processing

In the preferred embodiment of the invention, it is possible to compare profiles developed from a data set against profiles developed from a reference data set. Subsets of profiles may be compared as well. Profiles may be compared for any index code and profile reports may be output. It is also possible to identify those medical providers (whether individuals or institutions) who provide treatment that does not fall within the statistically established treatment patterns or profiles. Further, various treatment patterns for a particular diagnosis can be compared by treatment cost and patient outcome to determine the most effective treatment approach. Based on historical treatment patterns and a fee schedule, an accurate model of the cost of a specific medical episode can be created.

Figure 15:
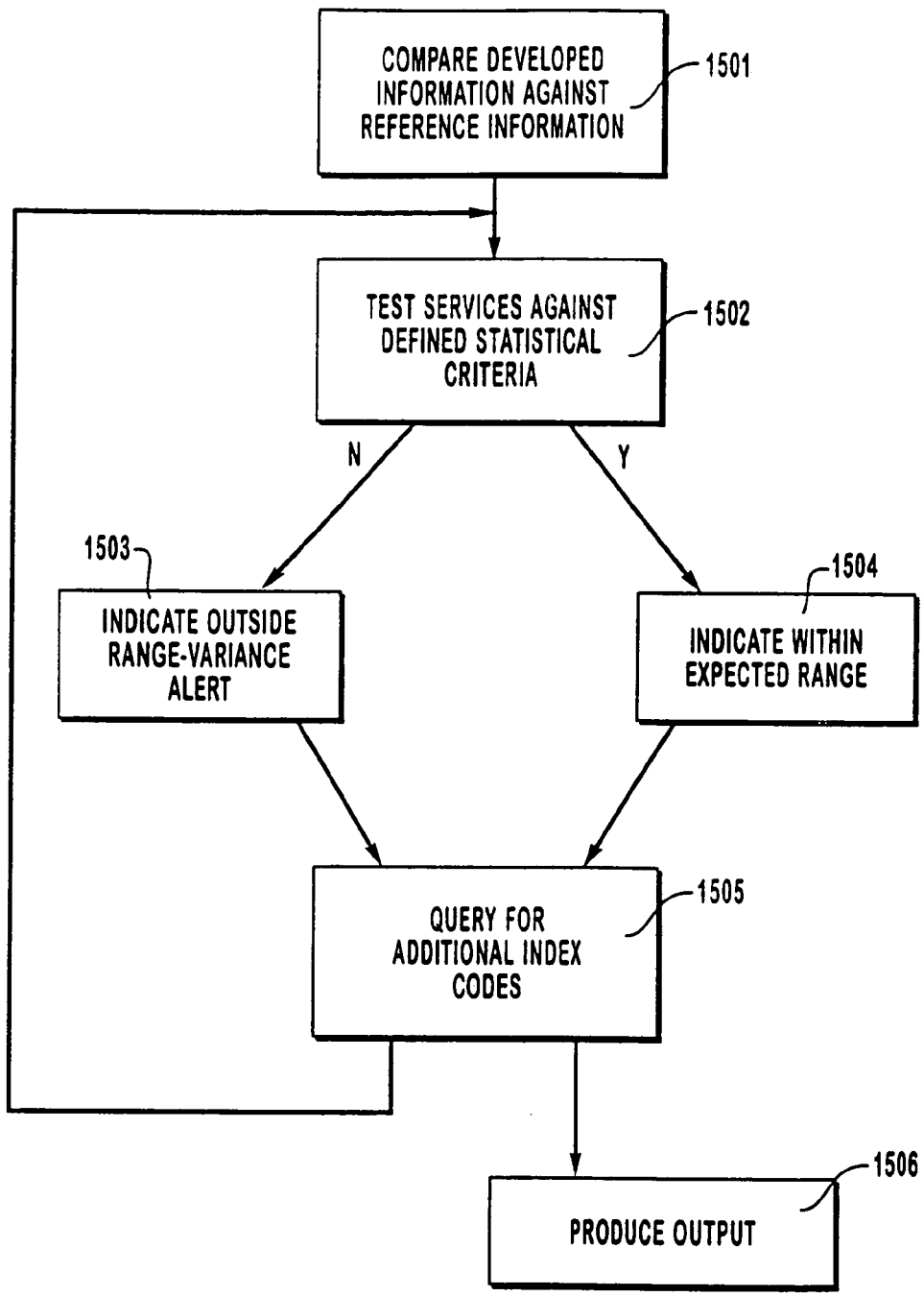
FIG. 15 depicts the process of the preferred embodiment of the Profile Comparison element of the invention.

The specific process of Comparison Processing is shown in FIG. 15 and described as follows. The first step, 1501, is the comparison of information developed from the data history search process with reference information stored in the Parameter Tables. The next step, 1502, is to test the services from the history processing to see if it falls within the defined statistical criteria in the Parameter Tables. If it does an indicator is given to this effect, 1504. If the services fall outside the statistical criteria of the reference Parameters Table, a variance alert describing the difference will be given, 1503. The process may be repeated for each index code and its profile developed in the history process, 1505. The final step is to produce output reports, 1506. These reports are either on-line look-up process reports or hardcopy report format reports.

3. Reporting

Reporting of various information contained in the database is provided in the preferred embodiment. Six different types of reports or displays are provided in the preferred embodiment, these are: Provider Practice Profile Report, Profile Comparison Reports, Resident Parameters Display, Local Parameters Display, Parameter Comparison Report and Chronological Forecast. Each of these reports or displays is described as follows.

The Provider Practice Profile Report is a set of reports which provide a tally or summary of total CPT and/or ICD code utilization by a provider or group of providers during a specified time interval and allows comparison against provided reference data or client generated reference data.

The select criteria for running the tally can be any one of the following:
- single physician, department, specialty or clinic by CPT and/or ICD
- multiple physicians, departments, specialties, or clinics by specialty, region, CPT and/or ICD
- period of time being analyzed Included in the report is the following:
- criteria for select
- claims analyzed
- average lines per bill
- invalid CPTs and percent of total for study
- invalid ICDs and percent of total for study
- incomplete ICDs and percent of total for study
- patients in age categories
- patients by gender
- missing ICDs and percent of total for study The report includes numerous (up to about 22 in the preferred embodiment) separate procedure (such as CPT) categories which are headers for each page. Each CPT utilized within that category will be reported by:
- frequency and percent of total
- dollar impact and percent of total for single or multiple fee schedules and/or allowable reimbursement schedules
- grand total if more than a single physician report The report includes a tally by ICD. Each ICD utilized is reported on by:
- frequency and percent of total
- dollar impact and percent of total for single or multiple fee schedule and/or allowable reimbursement schedules (dollar impact based on each line item CPT correlated to the ICD)

If a report includes region and/or specialty, there are numerous tallies for procedure categories and/or ICD.

The Profile Comparison Reports give the client a comparison of a health care provider's (or group of providers') utilization of CPT and/or ICD-9 codes in a specific episode of care against a reference set of utilization profiles. This includes number, frequency and chronological order of services along with other statistical information (eg, range, mode, confidence interval, etc.).

The comparison can be against one of the following:
- national norms resident in the tables
- regional norms resident in the tables
- client established norms developed by use of the tally report, outlined above
- other Selection criteria include the following:
- single physician, department, clinic or specialty by CPT and/or ICD to be compared against national, regional, specialty, and/or client established norms
- multiple physicians, departments, clinics, or specialties by CPT and/or ICD by specialty and/or region, to be compared against national, region, specialty, and/or client established norms
- set period of time being analyzed General information included in the report includes:
- criteria for select (i.e., national, regional, specialty, and/or client established)
- claims analyzed
- average lines per bill
- invalid CPTs and percent of total for study and comparison
- invalid ICDs and percent of total for study and comparison
- incomplete ICDs and percent of total for study and comparison
- patients in age categories and comparison
- patients by gender and comparison
- missing ICDs and percent of total for study and comparison The report includes numerous separate CPT categories which are headers for each page. Each CPT utilized within that category will be reported by:
- frequency and percent of total
- dollar impact and percent of total for single or multiple fee schedules and/or allowable reimbursement schedules
- grand total if more than a single physician report The report includes a tally by ICD. Each ICD utilized is reported on by:
- frequency and percent of total
- dollar impact and percent of total for single or multiple fee schedule and/or allowable reimbursement schedules (dollar impact based on each line item CPT correlated to the ICD)

If a report includes region and/or specialty, there are numerous tallies for CPT categories and/or ICD.

The Resident Parameters Display provides the client a look-up mode for information stored in the Practice Parameter Tables or client generated parameter tables. This lookup should be on the computer screen or as a print out.

The selection criteria is based on the key elements of the Practice Parameter tables. For Example:
  Index code for associated CPT codes and/or any other the following:
    index code only
    index code and indicators (i.e, related, complicating, rule/outs, symptoms, etc)
    specialty
    region
    age
    gender
    standard length of Episode of Care
    based on profile (tally)
    based on parameter (timeline)
  regional variables
  other misc. look-ups
    geozips incorporated in a region
    CPT for follow up days and/or lifetime occurrence
    specialty and associated CPT codes
    ICD and Risk Factor The Local Parameters Display provides the same information as described in the Display of Resident Parameters listed above.

The Parameter Comparison Reports are a set of reports which give the client a comparison of a physician (or group of physicians) utilization of CPT and/or ICD against an existing set of utilization norms over a timeline and in chronological order.

The comparison can be against one of the following:
  national norms resident in the tables
  regional norms resident in the tables
  client established norms developed by use of the tally report, outlined above
  other Selection criteria include the following:
  single physician, department, clinic or specialty by CPT and/or ICD to be compared against national, regional, specialty, and/or client established norms
  multiple physicians, departments, clinics, or specialties by CPT and/or ICD by specialty and/or region, to be compared against national, region, specialty, and/or client established norms
  set period of time being analyzed General information included in the report includes:
  criteria for select (i.e, national, regional, specialty, and/or client established)
  claims analyzed
  average lines per bill
  invalid claims due to incomplete Episode of Care
  invalid CPTs and percent of total for study and comparison
  invalid ICDs and percent of total for study and comparison
  incomplete ICDs and percent of total for study and comparison
  patients in age categories and comparison
  patients by gender and comparison
  missing ICDs and percent of total for study and comparison The report includes numerous separate procedure categories which are headers for each page. Each procedure category utilized within that category will be reported by:
  frequency and percent of total
  dollar impact and percent of total for single or multiple fee schedules and/or allowable reimbursement schedules
  grand total if more than a single physician report The Chronological Forecast provides statistical trend analysis and tracking of the utilization of billing codes representative of services performed by a physician for a given diagnosis over a set period of time and stored in chronological order. It will provide a summation of billed codes representative of services and diagnoses utilized by an entity over a period of time.

C. System Requirements

The method and system of this invention may be implemented in conjunction with a general purpose or a special purpose computer system. The computer system used will typically have a central processing unit, dynamic memory, static memory, mass storage, a command input mechanism (such as a keyboard), a display mechanism (such as a monitor), and an output device (such as a printer). Variations of such a computer system could be used as well. The computer system could be a personal computer, a minicomputer, a mainframe or otherwise. The computer system will typically run an operating system and a program capable of performing the method of the invention. The database will typically be stored on mass storage (such as a hard disk, CD-ROM, worm drive or otherwise). The method of the invention may be implemented in a variety of programming languages such as COBOL, RPG, C, FORTRAN, PASCAL or any other suitable programming language. The computer system may be part of a local area network and/or part of a wide area network.

Figure 16:
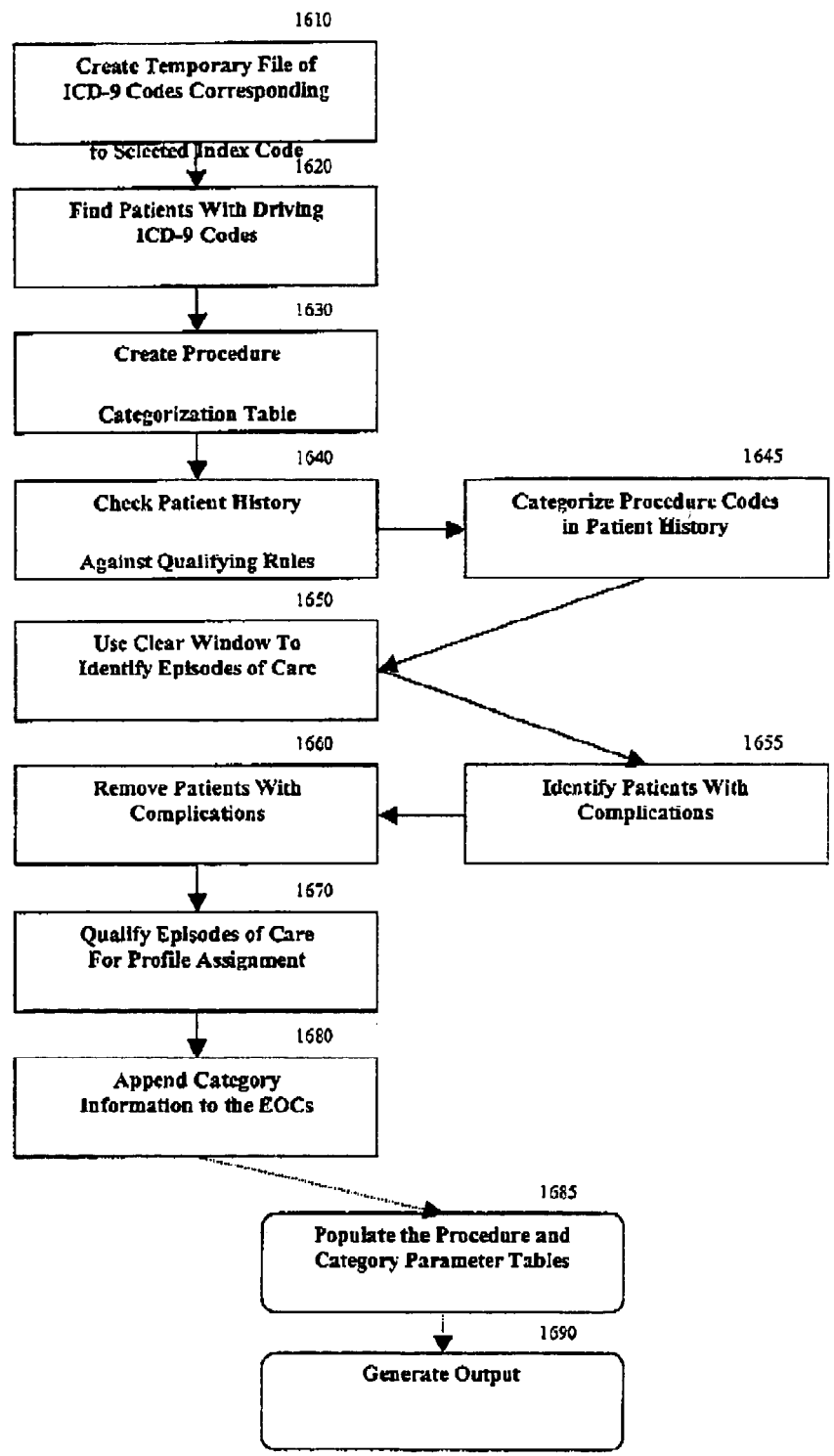
FIG. 16 depicts an alternative method for determining episodes of care for a selected medical episode.

Referring to FIG. 16 of the drawings and to the Microfiche Appendix, there is illustrated a second embodiment of a method for implementing the present invention for determining episodes of care for a selected medical condition identified by an Index Code. This embodiment is essentially the same as that described above except where noted, and the same nomenclature and tables will be referred to as in the above embodiment. The method is implemented by the computer program module pp_comp.4gl, which appears in the Microfiche Appendix.

a) Create Temporary File of ICD-9 Codes Corresponding to Selected Index Code

First, at step 1610, a temporary file, tmp_index, is created as a programming convenience, based on the Index Code for which episodes of care are being built. An Index Code identifies a medical condition (e.g., 174? might be the Index Code for the disease, Malignant Neoplasm of Female Breast). In the Index Detail Table, each Index Code is associated with ranges of ICD-9 diagnosis codes relevant to the medical condition, as well as separate Indicator values associated with each range. Only ICD-9 codes with an Indicator value of "I" or "MI" for the associated Index Code are used to drive the creation of an episode of care.

At 1610, the pp_comp.4gl module, after defining program variables, executes the function, lMake_index, which builds the temporary file, tmp_index, that contains a separate record for each ICD-9 code in the ranges of ICD-9 codes associated with the selected Index Code. (The value of the selected Index Code is passed to lMake_index in the variable ir.index, which contains the Index Code value provided in the input record for pp_comp.4gl, e.g., index_detail.index) The function call to the lMake_index appears at the bottom of page 2 of the pp_comp.4gl program listing.

The lMake_index function creates the tmp_index file by extracting from the Index Detail table and the Index Global table information that includes the ranges of ICD-9 codes associated with the selected Index Code and the Indicator value for each of such ICD-9 codes. For example, if, in the Index Detail table, Index Code 174? were associated with the following ranges of ICD-9 codes and Indicator values: 1740 to 1749 for Indicator "I"; 174 for Indicator "MI"; 61172 (Lump Or Mass In Breast) for Indicator "R;" then the tmp_index file records correlating to Index Code 174? would include the following information:

| Indicator | ICD9 |
|---|---|
| I | 1740 |
| I | 1741 |
| I | 1742 |
| I | 1743 |
| I | 1744 |
| I | 1745 |
| I | 1746 |
| I | 1747 |
| I | 1748 |
| I | 1749 |
| MI | 174 |
| R | 61172 | a) Find Patients with Driving ICD-9 Codes

Second, at step 1620, the raw data set that has undergone RAM processing is sorted by ICD-9 code to find all patient records having an occurrence of ICD-9 codes that may drive the creation of an episode of care for the selected Index Code (i.e., ICD-9 codes corresponding to ICD-9 codes in the tmp_index file having an Indicator value of "I" or "MI"). More specifically, the pp_comp.4gl module first creates a second temporary file, tmp_patient, with the following statement appearing at the top of page 3 of the source code listing.

select unique patient, relationship, sex
   from e_line lx, e_claim cx, tmp_index ix
   where ix.e_claim_id=cx.e_claim_id and
      lx.icd1=ix.icd9 and
      ix.indicator in ("I", "MI") and
      cx.e_claim_id !=0
   into temp tmp_patient This statement creates the temporary table, tmp_patient, and populates it with every unique combination of patient, relationship, and sex for every patient record containing an ICD-9 code listed in the tmp_index table with an Indicator value of "I", or "MI". Since tmp_index table maps Index Codes (medical conditions) to individual ICD-9 codes, the tmp_patient table identifies only those patients whose diagnoses in their medical claims history include one of the driving ICD-9 codes for the medical condition in question.

The program then creates a third temporary file, temp_data, and populates it with every record from the RAM-processed data set that meets two criteria:

(1) contains a combination of patient, relationship, and sex values that corresponds with a record in the tmp_patient table; and (2) contains an ICD-9 code that corresponds to an ICD-9 code in the tmp_index table.

The program statement that implements these two steps appears in the top half of page 3 of the pp_comp.4gl program listing in the select statement beginning "select cx.*, ix.date_of_serv, . . . " and ending with "into temp temp_data" Specifically, the following segment of the select statement links the e_claim table, which contains one record for each medical claim identified in the RAM-processed data set, to the tmp_patient table described above by matching the patient ID number, relationship code, and gender values in the two tables.

from e_line lx, e_claim cx, tmp_index ix, tmp_patient ip
   where lx.e_claim_d=cx.e_claim_id and
      lx.icd1=ix.icd9 and
      cx.patient=ip.patient and
      cx.relationship=ip.relationship and
      cx.sex=ip.sex and
   . . .

Next, the following segment of the select statement links the e_line table, which contains all records in the RAM-processed data set (that is, each claim line item that appears in the patients' medical histories), to the tmp_index table described above by matching the ICD-9 diagnosis codes in the two tables.

from e_line lx, e_claim cx, tmp_index ix, tmp_patient ip
   where lx.e_claim_d=cx.e_claim_id and
      lx.icd1=ix.icd9 and
   . . .

The result of the foregoing two steps is that the temp_data table will hold data that meet the following criteria:

1. The claim line items belong to a patient who had an "I" or "MI" somewhere in their medical history.
2. The claim line item includes an ICD-9 code that is also found in the tmp_index table.

At this point, the temp_data table holds claim line items that potentially will be included in an Episode of Care (EOC) for a selected Index Code.

a) Create Procedure Categorization Table

At 1630, the program creates another temporary table, cat_file that is used for grouping procedure codes into categories, which are described above in relation to the Category Table. The categories represent broad classes of treatment or service types, such as Major E and M (Evaluation and Management), Minor E and M, Major Diagnostic Radiology, Minor Diagnostic Radiology, Major Laboratory, and Major Therapeutic Surgery. Categories are used in place of individual procedure codes in subsequent program steps. For example, certain qualifying rules reference category codes rather than individual procedure codes. Also, categories are used to sort episodes of care into profile classes for analysis and reporting purposes.

At step 1630, the program assigns a category mnemonic (e.g., E for Major E and M) to each procedure code found in the temp_data file. This program step is implemented by the source code at pages 3–4, beginning with the statement "call errorlog ("Making Cat File")," through the statement, "create unique index i_catf1 on cat_file(proc);". Specifically, the cat_file table is built by looping through each procedure code in the temp_data table, finding every unique CPT/HCPCS code in that table and associating the code found with a category.

b) Check Patient History Against Qualifying Rules

At step 1640, the records from the patient histories (now in the temp_data table) are reviewed to ensure compliance with the patient-level qualifying rules defined by the various qualifying tables of the present invention. Patient records that fail to qualify are no longer considered for EOC evaluation for the selected Index Code. The pp_comp.4gl source code for implementing this step includes the statements beginning at the middle of page 4 with "declare upat_curs cursor for" and continuing through the bottom of page 5, "execute del_qual." Pertinent portions of these statements are reproduced below.

foreach upat_curs into q.*
   . . .
   call qual_check("P") returning passed, eoc_profile, rule_err
   if not passed then
      . . .

execute del_temp_data using prev_pat, prev_rel, prev_sex
. . .
end foreach

Generally, these program statements perform the following steps:
- read fields from each patient record in the temp_data table into upat_curs;
- for each patient record in upat_curs;
  - ➢ read the record into the variable set q.*;
  - ➢ call qual_check function to determine if the patient data on the record satisfies a set of patient qualifying rules, and
  - ➢ if not, remove all of the patient's data from further consideration for the selected Index Code.

These patient qualification steps are repeated until such processing has been completed for all patients having a record in the temp_data table.

The Qual_Check Function

The qual_check function identified above can be found beginning on page 13 of the pp_comp.4gl program listing, beginning with the statement "function qual_check(in_scope)" and continuing through the end of page 16. For the selected Index Code, the qual_check function loops through all entries in the qual_master (Qualifying Master) table where the Scope field is equal to the value passed to the qual_check function in the in_scope variable. (In the present embodiment, the in scope variable is set to either the value "E" or "P", which indicates whether the function checks for 'E' pisode or 'P'atient level qualifying rules.) Here, at step 1640, the value of the in_scope variable is set to 'P,' such that only patient level qualifying rules are executed.

Based on the value of the Group field in the Qualifying Master table for the selected Index Code, the qual_check function extracts qualifying rules information (i.e., Rule Type and Rule Identifier) from the qual_group (Qualifying Group) table. More particularly, when the qual_check function reads a record from the qual_master table for the selected Index Code, it uses the value of the rule_group field from the qual_master record as a parameter to a query for reading a record in the qual_group (Qualifying Group) table. Depending upon the value of the rule_type field this qual_group table record, the qual_check function executes a different set of program statements implementing qualifying logic. As will be set forth more fully below, the qual_check function uses this rule_type value to extract information for identifying the proper qualifying rules from either the Qualifying Index table or Qualifying Code table, identified in the program listing as qual_ic and qual_cc, respectively.

In the preferred embodiment described herein, the three values of the rule_type field that trigger execution of qualifying logic are "II", "IC", and "CC". "II"-type rules are qualifying rules specific to the Index Code and, for example, may require two or more occurrences of the Index Code in a patient history with different dates of service. "IC"-type rules define criteria for Index Codes relative to procedure (CPT) category codes. An "IC"-type rule_identify CPT categories (not specific CPT codes) for the specific Index Code. "CC"-type qualifying rules are similar to "IC" rules, but instead of checking for a certain number of one type of procedure category, the "CC"-type logic checks for a single occurrence of each of two separate procedure categories.

Pertinent portions of the qual_check function are reproduced below.

open mast_curs using in_scope
fetch mast_curs into qm.* let hold_status=status
while hold_status !=notfound
  open grp_crs using qm.rule_group
  fetch grp_curs into qg.*
  while status !=notfound
  . . .
  when qg.rule_type="II"
  . . .
  when qg.rule_type="IC"
  . . .
  when qg.rule_type="CC"
  . . .

Thus, depending on the value of the rule_type field, the program applies one of the sets of qualifying logic to determine whether a patient's record satisfies the appropriate set of qualifying rules for that patient.

Type II Qualifying Rules

The program logic for Type II qualifying rules begins by building a SQL query to check the patient record for a certain number of occurrences of specific codes (ICD-9, CPT, HPCPS or category) or Indicator values. The requisite number of occurrences of codes or Indicator values for the particular rule_type is stored in the Number required field (qg.num_required) of the Qualifying Group table. Upon execution of the query, and if the requisite number of occurrences is found, the qual_check considers the patient to have successfully passed the Type II qualifying rules.

More particularly, the Type II program logic builds a SQL query based on values read from the qual_ic table using the values of rule_type and rule_id read from the qual_group table. If the cat_cpt field of the qual_ic record is populated (with a category, CPT, HCPCS, or ICD value), the where clause of the SQL statement is expanded to create a statement that checks for a match between the icd1 field (from the tmp_index table) and the value of cat_cpt. If cat_cpt is not populated, the where clause looks for a match between the indicator field in the tmp_index table and the value read from the indicator field in the qual_ic table. This process continues for every record in the qual_ic table containing the rule_type value read from the qual_group table.

When no more records exist in the qual_ic table for the given rule_type, the SQL statement that was constructed is executed, and the number of records returned is tallied. The total number of records satisfying the SQL query is then compared against the value of the num_required field from the qual_group table. If the total exceeds the value of the num_required field, the rule is identified as having "passed"; if not, the rule is "failed".

Next, the logical field from qual_group table is read. The logical field indicates whether the qualifying rule is inclusive or exclusive in nature. If the value of the logical field is "F", the rule_passed variable is inverted (that is, if the rule is exclusionary, and the requisite number of occurrences have been found, then rule was not "passed," and vice versa). Once this step is complete, the qual_check function checks the rule_passed value to determine whether to continue checking the patients' records for qualifying circumstances, or stop processing the patients' records and return control to the main program pp_comp.4gl. If the value of rule_passed for the patient's record is not "true", the qual_check program exits and returns the rule_passed value back to the section of pp_comp.4gl code that called this qualifying logic.

Type IC Qualifying Logic

Similar to the Type II qualifying logic, the Type IC logic initially reads a record from the qual_ic table using the rule_type and rule_id values previously retrieved from the qual_group table. For each relevant record in the qual_ic table, the program counts the number of records in the temp_qual table where the category field matches the cat_cpt field value found on the qual_ic record. This count is then compared against the num_required field value from qual_group. If the count is greater than or equal to num_required, the Type IC logic sets the rule_passed variable to "true" (and, as was set forth above for the Type II logic, inverts its value where the value of the logical field is "F"). The qual_check function then checks the rule_passed value to determine whether to continue checking the patients' records for qualifying circumstances. If the value of rule_passed for patient's record is not "true", the qual_check program exits and the rule_passed value is returned the main program.

Type CC Qualifying Logic

The Type CC qualifying logic differs from the Type II and IC logic in that it obtains its qualifying rule information from the qual_cc (Qualifying Code) table rather than qual_ic (Qualifying Index) table. For each record in qual_cc matching the rule_type and rule_id from qual_group the following steps occurs:

1. The number of records in temp_qual where the category field matches the value in the cat_cpt1 field from qual_cc is tallied.
2. If this count is greater than or equal to 1, the number of records in temp_qual where the category field matches the value in the cat_cpt2 field from qual_cc is tallied. If it is not, the Type CC code skips to the logic segment in step 4 (below).
3. If the count is less than the value of the num_required field from qual_group, the logical field from qual_group is checked, and if the value of logical is "T", the passed variable is set to "false". The passed variable is also set to "false" if the count is not less than the value of the num_required field and the value of logical is "F." (If the count is not less than num_required, the code skips to the logic in step 4.)
4. If the passed variable is false, the section of code exits and passes control back to the area of the program that called this logic; otherwise the program checks for another relevant record in the qual_cc table.
5. When no more relevant records exist in qual_cc, this section of code exits and returns control back to the area of the program that called this logic, returning the value of the passed variable to the main program (as in the Type II and Type IC logic segments).

In each of the aforementioned qualifying logic segments, the qual_check function evaluates whether the qualifying logic is considered "passed" or "failed." If the rule is considered "failed," then the records for the patient currently being processed have been disqualified for further processing for the selected Index Code. The function continues processing with the next patient. When no more patients remain, the qual_check function returns control back to the main body of the pp_comp.4gl program.

a) Categorize Procedure Codes in Patient History

Additionally, at 1645, as part of the foreach loop that calls the qual_check function, the program executes the following two statements appearing at the bottom of page 4 and continuing to page 5, which determine categories for the procedures codes appearing in each patient record and append a category code to the patient record:

open get_cat using q.cpt
fetch get_cat into q.category

The category codes are used by the qual_check function as part of qualifying patients for episode of care creation, at 1640, and sorting episodes of care into profile classes, at 1680.

B) Use Clear Window to Identify Episodes of Care

After processing each patient history against the applicable qualifying rules, the program, at step 1650, begins to build episodes of care for patient histories that did not fail the qualifying rules. A clear window time period delimits the onset and resolution of an episode of care. The clear window time period is selected for a specific Index Code from the Window Table.

In the pp_comp.4gl program, the function call on page 6 to report r_edit begins clear window processing.

finish report r_edit

The report r_edit function (appearing on pages 8 and 9 and reproduced in pertinent part below) identifies the proper clear window time period, flags (for later processing) records indicating a medical complication, and then applies the clear window period to identify discrete episodes of care.

```
report r edit (c, l, i, cur__by)
    output
    . . .
        order by c.patient, c. relationship, c.sex, l.date of serv
    . . .
        select beg win into win max
            from window
            where staging in
                (select staging from index where index =
    ir.index)
```

First, report r_edit function sorts the claim line item records by patient, relationship, sex and date of service. The report r_edit function then determines the proper clear window period for the selected Index Code (which index corresponds to the ICD-9 codes appearing in the line item records now being processed). The beg_win (Beginning Window) field of the window (Window) table defines the clear window period, win_max, that is, the maximum number of days without the occurrence of a service relating to a given medical condition (Index Code) that defines the beginning of a new episode of care. The report r_edit function identifies the appropriate record in the Window Table from which to extract the Beginning Window value by matching the Staging values in the Index Table record for the selected Index Code with the Staging Indicator in the Window Table record for the selected Index Code. In the Index Table, each Index Code is associated with a Staging value. In the Window Table, each unique combination of Index Code and Staging Indicator value is associated with a Beginning Window size.

In addition, at 1655, patient records identified with a complicating diagnosis code are tallied (and flagged to be removed from EOC processing later, at step 1660). Specifically, in the following segments of the report r_edit function (on page 11 of the program listing), each line item for every patient record in the temp_data table is checked for ICD-9 codes corresponding to an ICD-9 code having an Indicator value "C" (from the tmp_index table) and any such records are flagged.

open cnt_complic using l.icd1
fetch cnt_com;lic into ok_flag
close cnt_complic
if ok_flag then
. . .

```
    if not cur_eoc_is_bad then
        let eoc_comp=eoc_comp+1
        let an_eoc_was_bad=true
        let cur_eoc_is_bad=true
        let cur_status="C"
    end if
end if
```

Following the flagging of complications at 1655, the program then proceeds sequentially through the claim line item records in the temp_data table (on a patient-by-patient basis) and identifies whether or not the applicable clear window period has expired between any two consecutive records. This algorithm uses the win_max variable that was populated earlier in step 1650 with the proper Beginning Window value for the ICD-9 code on the record. The date of service in each record is compared with the date of service in the record immediately preceding it chronologically. If the two records being compared are separated by a time period equal to, or greater than, the clear window period (win_max), the later record is identified as the beginning event of the a new episode of care. This iterative process is continued for all remaining line item records for all patient claims and is implemented by the following segments of the report r_edit function (appearing on page 11):

```
    if l.date_of_serv-prev_dos>=win_max then
    . . .
        let eoc_cnt=eoc_cnt+1
        let cur_eoc_is_bad=false
        let eoc_cnt_for_pat=eoc_cnt_for_pat+1
        let cur_eoc_num=cur_eoc_num+1
        let cur_status="V"
    end if
    let prev_dos=l.date_of_serv
```

An alternative embodiment, not implemented in the Microfiche Appendix, can employ a second process to delineate potential episodes of care. In such embodiment, the Window table is populated with values in both the Beginning Window and Ending Window fields. The Ending Window defines a post-episode clear window period, which may be different from the pre-episode clear window (Beginning Window). In this manner, an episode of care can be defined relative to asymmetrical clear window time periods.

In the present embodiment, after the program checks that the clear window period has not been exceeded, the claim line item is associated with a potential episode and inserted into the eoc table. Once all line items are so processed, the eoc table replaces temp_data as the repository for all patient claims detail information and is used for all further processing.

c) Remove Patients with Complications

At step 1660, the program removes from further consideration patients having complications in their medical claims history, as indicated by a flag referred to above in step 1655. Namely, all records for patients flagged as having complications are deleted from the eoc table. This step is subsumed within the program statements for the report r_edit function. More particularly, the statement "put ins_pat_eoc" inserts the patient, relationship, and sex values for patients identified with complications into a temporary table, pat_eoc, as specified in the following code, found on page 9 of the program listing:

```
    create temp table pat_eoc (
    patient char(15),
    relationship char(1),
    sex char(1)) in userspace1;
    declare ins_pat_eoc cursor for
        insert into pat_eoc values (c.patient, c.relationship, c.sex)
    open ins_pat_eoc
```

The following program segment, found on page 6 of the pp_comp.4gl program listing, deletes every record from the eoc table containing a patient, relationship and sex combination listed in the pat_eoc table, thus removing all of the records for every patient who was considered as having complications for the stated medical condition:

```
    prepare del_comp_eoc from
        "delete from eoc where e_claim_id=?"
    call errorlog ("updating Comp Patients")
    declare comp_pat_curs cursor for
    select unique e_claim_id
        from e_claim cc, pat_eoc pe
        where cc.patient=pe.patient and
            cc.relationship=pe.relationship and
            cc.sex=pe.sex
    . . .
    foreach comp_pat_curs into c.e_claim_id
    . . .
        execute del_comp_eoc using c.e_claim_id
    end foreach
    . . .
    call errorlog ("done with comp Patients")
```

Thus, at this step, all records for patients having a complication flagged in their medical claims history are deleted from the eoc table and removed from further consideration for episode or profile building.

d) Qualify Episodes of Care For Profile Assignment

At step 1670, each potential episode of care in the eoc table is checked against EOC qualifying rules to determine whether the episode will be assigned to a profile. Episodes that fail the qualifying rules are not removed from the eoc table; but neither are they assigned a profile. Step 1670 is implemented in pertinent part by a foreach statement that loops through each record in the eoc table, which, as mentioned previously, now contains all claims line item records that have been found to be part of a valid episode of care.

The following statements (including the foreach statement) appears in the pp_comp.4gl program listing beginning on page 7:

```
    open qual_ins
    let icount=0
    foreach geoc_curs into cur_eoc_num, q.date_of_serv, q.cpt, q.icd1
    . . .
        let q.category=" "
        open get_cat using q.cpt
        fetch get_cat into q.category
        if icount=0 then
            let prev_eoc=cur_eoc_num
        end if
    . . .
        if cur_eoc_num !=prev_eoc then
            close qual_ins
            let eoc_profile=" "
            call qual-check("E") returning passed, eoc_profile, rule_err
            execute upd_eoc using eoc_profile, prev_eoc
    . . .
            open qual_ins
            let prev_eoc=cur_eoc_num
        end if
        put qual_ins
``` end foreach Before invoking the foreach statement, the program begin by opening a temporary table, qual_ins, that is used for storing a patient's records based on the results of the qualification process (that is, the qual_check function). Thereafter, the foreach loop is begun. In the foreach loop, an if/else conditional is used to determine whether the record being processed is the first patient record in the eoc table, and if so, initializes the prev_eoc variable to the current EOC number. Thereafter, the qual_check function is invoked with a value of "E" in the in_scope variable, which indicates that episode qualifying rules are to be used by the function.

As is set forth in detail in Section (d) above, the qual_check function executes different logic based on the type of qualifying rules that are associated with the selected Index Code. For episode qualification, the same three sets of qualifying logic (Type II, Type IC, Type CC) are employed as in the patient qualification process, except that access to the qualifying tables (and rules) is determined by the scope value "E" rather than "P". Again, the qualifying rules are defined by the contents of the same set of four qualifying tables—the Qualifying Master, Qualifying Group, Qualifying Index, and Qualifying Code tables. For episodes of care, however, the qualifying rules determine if a potential EOC meets the minimum profiling criteria expected for the selected Index Code (e.g., episode includes procedure codes indicating surgical services required for the medical condition).

As compared with its operation in the patient qualification process set forth above, when executed for episode qualification, the qual_check function evaluates whether the qualifying logic only until the first set of rules are "passed." If any rule is considered "passed," then the episode currently being processed has qualified for profiling. The qual_check function discontinues episode qualification and returns control back to the pp_comp.4gl program. In addition to the rule_passed value, the qual_check function returns to the main program a value in the eoc_profile variable, which profile number (profile_num) is then inserted into the eoc table. The qual_check function sets the value of eoc profile to equal the contents of the Profile field of the Qualifying Master table (qm.profile). If the episode of care does not satisfy the qualifying criteria, the eoc_profile variable the episode is not assigned a profile. Thus, the qual_check function not only determines whether the episode may profiled but also to which profile it belongs.

The profiles assigned to episodes correspond to combinations of treatment patterns that are likely to arise for a given medical condition. There are eight basic profile classes to which an episode of care may be assigned. The profile classes identify common combinations of treatment patterns that are useful for statistically analyzing and reporting on medical provider billing data. These Profile Classes are:

0. Common Profile (diagnostic and E/M services common to all of the above).
1. Surgery/Medicine/Radiation Profile
2. Medicine/Radiation Profile
3. Surgery/Radiation Profile
4. Surgery/Medicine Profile
5. Radiation Profile
6. Medicine Profile
7. Surgery Profile e) Append Category Information to the EOCs After all valid EOCs have been assigned to a profile, processing continues at step 1680 with appending category data to the eoc table records. Specifically, at step 1680, all of the CPT codes in the eoc table records are categorized using the cat_file table created at step 1645. This step involves the re-categorization of all CPT codes but only in the patient records that have been qualified for episode of care creation during the previous program step 1670. The functionality is similar to that in step 1670; the difference being that in step 1680, the category code is appended to the eoc table record, whereas in step 1670, the category code is held temporarily in a variable to assist in the EOC profile categorization. (During execution of the foreach loop of step 1670, the program performs a lookup on the category table based on the procedure code of the medical record in question to assist in the profile categorization of an episode.) In an alternative embodiment, not implemented in the Microfiche Appendix, the eoc table with category information appended is then used to populate the procedure and category parameter tables, which store historical billing and statistical information by Index Code.

f) Populate the Procedure and Category Parameter Tables

In the above-referenced alternative embodiment, at step 1685, data from qualified eoc table records (that now include category codes) is added to the procedure and category parameter tables. In general, data from all of the episodes of care for each Index Code are inserted into parameter tables to allow for summary statistical profiling.

g) Generate Output

In yet another embodiment, statistical profiles and other analysis of the data from all episodes of care are provided through the generation of output reports, 1690. The output reports may be implemented as an online table look-up or a hard copy report.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

We claim:

1. A computer-implemented process for processing medical claims including the steps of:
   (a) reading a medical claim data, input as at least one of a plurality of data records, into a computer memory;
   (b) validating each of the at least one of a plurality of data records for at least one of a diagnosis code and a treatment code;
   (c) reading at least one pre-defined relationship between the at least one of a diagnosis code and a treatment code in the validated at least one of a plurality of data records and pre-defined episode treatment categories; and
   (d) grouping the validated at least one of a plurality of data records to an episode treatment category based upon the pre-defined relationship, each episode treatment category having a dynamic time window defining a time period which validated at least one of plurality of data records may be grouped to an episode treatment category.

* * * * *